(12) United States Patent
Schwede et al.

(10) Patent No.: US 9,717,739 B2
(45) Date of Patent: Aug. 1, 2017

(54) 17-HYDROXY-17-PENTAFLUOROETHYL-ESTRA-4,9(10)-DIEN-11-ARYL DERIVATIVES, METHOD OF PRODUCTION THEREOF AND USE THEREOF FOR THE TREATMENT OF DISEASES

(71) Applicant: Bayer Intellectual Property GmbH, Monheim (DE)

(72) Inventors: Wolfgang Schwede, Glienicke (DE); Ulrich Klar, Berlin (DE); Carsten Moller, Berlin (DE); Andrea Rotgeri, Berlin (DE); Wilhelm Bone, Berlin (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/731,232

(22) Filed: Jun. 4, 2015

(65) Prior Publication Data

US 2015/0342962 A1     Dec. 3, 2015

Related U.S. Application Data

(63) Continuation of application No. 13/376,512, filed as application No. PCT/EP2010/004149 on Jul. 7, 2010, now abandoned.

(30) Foreign Application Priority Data

Jul. 20, 2009 (DE) .......................... 10 2009 034 362

(51) Int. Cl.
    *A61K 31/567*      (2006.01)
    *C07J 41/00*      (2006.01)
    *C07J 31/00*      (2006.01)

(52) U.S. Cl.
    CPC ........... *A61K 31/567* (2013.01); *C07J 31/006* (2013.01); *C07J 41/0083* (2013.01)

(58) Field of Classification Search
    CPC .... C07J 41/0083; C07J 31/006; A61K 31/567
    USPC ................................ 514/171, 179; 552/648
    See application file for complete search history.

(56) References Cited

U.S. PATENT DOCUMENTS

| 6,172,052 B1 | 1/2001 | Cook et al. |
| 2005/0143364 A1 | 6/2005 | Kim et al. |
| 2012/0149670 A1 | 6/2012 | Schwede et al. |

OTHER PUBLICATIONS

Furmann et al., J. Med Chem 2000, 43, 5010-5016.
Nozaki et al, Soyaku Kagaku, Kagakudojin, 1995, pp. 98-99.

*Primary Examiner* — Barbara P Badio
(74) *Attorney, Agent, or Firm* — Nixon & Vanderhye P.C.

(57) ABSTRACT

The invention relates to 17-hydroxy-17-pentafluoroethyl-estra-4,9(10)-dien-11-aryl derivatives of Formula I with progesterone antagonizing action and method of production thereof, use thereof for the treatment and/or prophylaxis of diseases and use thereof for the production of medicinal products for the treatment and/or prophylaxis of diseases, in particular of fibroids of the uterus (myomas, uterine leiomyoma), endometriosis, heavy menstrual bleeds, meningiomas, hormone-dependent breast cancers and complaints associated with the menopause or for fertility control and emergency contraception.

14 Claims, No Drawings

17-HYDROXY-17-PENTAFLUOROETHYL-ESTRA-4,9(10)-DIEN-11-ARYL DERIVATIVES, METHOD OF PRODUCTION THEREOF AND USE THEREOF FOR THE TREATMENT OF DISEASES

The invention relates to 17-hydroxy-17-pentafluoroethyl-estra-4,9(10)-dien-11-aryl derivatives of Formula I with progesterone antagonizing action and method of production thereof, use thereof for the treatment and/or prophylaxis of diseases and use thereof for the production of medicinal products for the treatment and/or prophylaxis of diseases, in particular of fibroids of the uterus (myomas, uterine leiomyoma), endometriosis, heavy menstrual bleeds, meningiomas, hormone-dependent breast cancers and complaints associated with the menopause or for fertility control and emergency contraception.

These compounds are valuable pharmaceutical active substances. They can be used among other things for the production of pharmaceutical preparations for the treatment of fibroids of the uterus or endometriosis, heavy menstrual bleeds, meningiomas, hormone-dependent breast cancers and of complaints associated with the menopause or for fertility control and emergency contraception. For the treatment of fibroids of the uterus and endometriosis, the compounds according to the invention can also be administered sequentially in combination with gestagens. In such a treatment regimen the compounds according to the invention could be administered over a period of 1-6 months, followed by a pause in treatment or sequential treatment with a gestagen over a period of 2-6 weeks or followed by treatment with an oral contraceptive (OC-combinations) over the same period.

The efficacy of the compounds according to the invention as progesterone receptor antagonist was demonstrated in vitro in transactivation tests and in vivo in the rat (termination of early pregnancy). Compounds with antagonistic action on the progesterone receptor (competitive progesterone receptor antagonists) became known for the first time in 1982 (RU 486; EP57115) and many of them have been described since then. Progesterone receptor antagonists with a fluorinated 17α-side chain were published in WO 98/34947 and Fuhrmann et al., J. Med. Chem. 43, 5010-5016 (2000).

The compounds with fluorinated 17α-side chain described in WO 98/34947 generally have a very strong antagonistic activity on the progesterone receptor. Compounds that are very potent and therefore preferred in WO 98/34947 are 11β-(4-acetylphenyl)-20,20,21,21,21-pentafluoro-17-hydroxy-19-nor-17α-pregna-4,9-dien-3-one, 11β-(4-acetylphenyl)-20,20,21,21,21-pentafluoro-17-hydroxy-19-nor-17α-pregna-4-en-3-one and 6'-acetyl-9,11β-dihydro-17β-hydroxy-17α-(1,1,2,2,2-pentafluoroethyl)-4'H-naphth[3',2',1':10,9,11]ester-4-en-3-one. These compounds are transformed to a considerable extent in vivo to various metabolites, some with strong, and others with reduced pharmacological activity.

Metabolism occurs mainly on the 4-substituent of the 11-phenyl residue. Compounds are described in WO 2008/058767 that are, at least partly, metabolites of the compounds described in WO 98/34947. The problem to be solved by the present invention is to make highly potent competitive progesterone receptor antagonists available and thus create alternatives for the treatment of gynaecological diseases.

It was found that the compounds according to the invention are especially suitable for solving this problem. In particular, compounds with alkylsulphanyl and alkylsulphonyl groups show very strong antagonistic activity on the progesterone receptor, i.e. they inhibit the action of progesterone on its receptor.

It was also found that the compounds with alkylsulphonyl groups, compared e.g. with alkanoyl groups, have a far higher metabolic as well as chemical stability against temperature, light and oxidative stress.

For example, the compound (11β,17β)-17-hydroxy-11-[4-(methylsulphonyl)phenyl]-17-(pentafluoroethyl)estra-4,9-dien-3-one (example 4) displays, compared with the respective analogue with an alkanoyl or hydroxyalkanoyl group (11β,-(4-acetylphenyl)-20,20,21,21,21-pentafluoro-17-hydroxy-19-nor-17α-pregna-4,9-dien-3-one or 20,20,21,21,21-pentafluoro-17-hydroxy-11β-[4-(hydroxyacatyl)phenyl]-19-nor-17β-pregna-4,9-dien-3-one), a surprisingly high stability under thermal load, under the influence of UV light and a surprisingly low oxidation sensitivity.

Compounds with an alkylsulphonimidoyl group in position 4 of the 11-phenyl ring have, despite sometimes lower in vitro activity, a very strong action in vivo. These compounds are at least partially prodrugs of the corresponding sulphones, and the compounds with an alkylsulphonimidoyl group have markedly better solubility in water.

It is also surprising that both compounds with an alkylsulphonyl group, and compounds with alkylsulphonimidoyl groups, especially the corresponding methyl compounds, have a low inhibition potential with respect to the investigated CYP-isoenzymes CYP1A2, CYP2C8, CYP2C9, CYP2D6 and CYP3A4, and up to a maximum concentration that is soluble or used in the assay (minimum 10 μM, maximum 20 μM), 50% inhibition was not reached in any case investigated.

These in vitro findings suggest, for the substances investigated, an especially low risk of interactions with co-administered medicinal products with respect to CYP-inhibition.

Moreover, for (11β,17β)-17-hydroxy-11-[4-(methylsulphonyl)phenyl]-17-(pentafluoroethyl)estra-4,9-dien-3-one, an especially favourable safety profile (in acute and chronic tests) was found in preclinical investigations on rodents and non-rodents.

The present invention relates to 17-hydroxy-17-pentafluoroethyl-estra-4,9(10)-dien-11-aryl derivatives with the general chemical formula I:

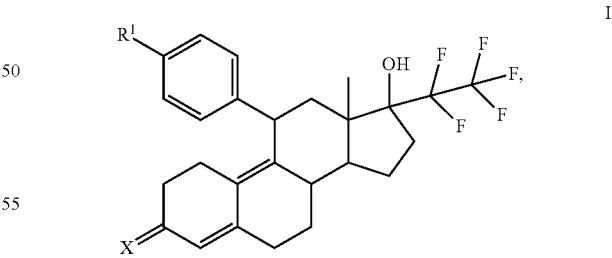

in which
R¹ stands either for a residue Y or for a phenyl ring substituted once or twice with a residue Y,
Y is selected from the group comprising $SR^2$, $S(O)R^3$, $S(O)_2R^3$, $S(O)(NH)R^3$, $S(O)(NR^4)R^3$, $S(O)_2NR^9R^{10}$,
$R^2$ represents hydrogen or $C_1$-$C_6$-alkyl or $C_7$-$C_{10}$-aralkyl or aryl,
$R^3$ $C_1$-$C_6$-alkyl or aryl,
$R^4$ a group $S(O)_2R^6$, $R^6$ phenyl or 4-methylphenyl X an oxygen atom, $NOR^7$ or $NNHSO_2R^7$ and $R^7$ is selected from the group comprising hydrogen, $C_1$-$C_{10}$-alkyl, aryl $R^9$, $R^{10}$ independently of one another are selected from the group comprising hydrogen, $C_1$-$C_{10}$-alkyl or aryl or alternatively represent, together with the nitrogen atom, a 3- to 8-membered, saturated or unsaturated heterocyclic ring and their salts, solvates or solvates of the salts, including all crystal modifications.

Depending on their structure, the compounds according to the invention of general formula I can exist in stereoisomeric forms (enantiomers, diastereomers). The invention therefore comprises the enantiomers or diastereomers and their respective mixtures including racemates. The stereoisomerically uniform constituents can be isolated in a known way from said mixtures of enantiomers and/or diastereomers.

Each of the stated substituents on the steroid backbone chain can be both in an α-position and in a β-position. Moreover, the substituents on the steroid backbone chain, which contain a double bond and in which the double bond on each atom bears at least one substituent, which is not hydrogen, can be both E- and Z-configured.

If the compounds according to the invention can exist in tautomeric forms, the present invention comprises all tautomeric forms.

Physiologically harmless salts of the compounds according to the invention are preferred as salts within the scope of the present invention. However, salts that are not suitable in themselves for pharmaceutical uses, but can for example be used for the isolation or purification of the compounds according to the invention, are also covered.

Physiologically harmless salts of the compounds according to the invention comprise—when they contain a basic function—salts with inorganic or organic acids, in particular of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalene-disulphonic acid, acetic acid, trifluoroacetic acid, propionic acid, lactic acid, tartaric acid, malic acid, citric acid, fumaric acid, maleic acid and benzoic acid.

Physiologically harmless salts of the compounds according to the invention comprise—when they contain an acid function—alkali metal salts, alkaline earth metal salts or ammonium salts, such as can be obtained by reaction with corresponding inorganic or organic bases. We may mention, for example and preferably, alkali metal salts (e.g. sodium and potassium salts), alkaline earth metal salts (e.g. calcium and magnesium salts) and ammonium salts, derived from ammonia or organic amines with 1 to 16 carbon atoms, such as, for example and preferably, ethylamine, diethylamine, triethylamine, ethyldiisopropylamine, monoethanolamine, diethanolamine, triethanolamine, bicyclo-hexylamine, dimethylamino-ethanol, procaine, dibenzylamine, N-methylmorpholine, arginine, lysine, ethylenediamine, N-methyl piperidine, N-methyl glucamine, D-methyl glucamine, ethyl glucamine, 1,6-hexadiamine, glucosamine, N-methylglycine, 2-amino-1,3-propandiol, tris-hydroxymethyl-aminomethane and 1-amino-2,3,4-butanetriol.

Those forms of the compounds according to the invention that display, in the solid or liquid state, adduct formation with solvent molecules, are designated as solvates within the scope of the invention. The solvent can be present in stoichiometric or even non-stoichiometric proportions. In the case of stoichiometric solvates, they are also called hemi-, (semi-), mono-, sesqui-, di-, tri-, tetra-, penta-, etc. solvates. Hydrates are a special form of solvates, in which the coordination takes place with water.

Moreover, the present invention also comprises prodrugs of the compounds according to the invention. The term "prodrugs" comprises compounds which, while they are in the body, are converted to compounds according to the invention, for example by enzymatic or hydrolytic processes.

Within the scope of the present invention, unless otherwise specified, the substituents have the following meaning:

Alkyl stands for linear or branched alkyl groups with 1-6 carbon atoms, for example methyl, ethyl, propyl, isopropyl, n-butyl, sec.-butyl, isobutyl, tert.-butyl, n-pentyl, isopentyl, neopentyl, hexyl, heptyl, octyl, nonyl and decyl.

Aryl stands for a mono- to tricyclic aromatic, substituted or unsubstituted carbocyclic residue, for example phenyl, naphthyl, which can be substituted one or more times with halogen (F, Cl, Br, I), OH, O-alkyl, $CO_2H$, $CO_2$-alkyl, $NH_2$, $NH(C_1$-$C_{10}$-alkyl), $N(C_1$-$C_{10}$-alkyl)$_2$, in particular $N(CH_3)_2$, $NO_2$, $N_3$, CN, $C_1$-$C_{10}$-alkyl, $C_1$-$C_{10}$-perfluoro-alkyl, $C_1$-$C_{10}$-acyl, $C_1$-$C_{10}$-acyloxy groups.

Heteroaryl stands for an aromatic, mono- or bicyclic residue with as a rule 5 to 10, preferably 5 to 6 ring atoms and up to 5, preferably up to 4 heteroatoms from the series S, O and N, for example and preferably for benzofuranyl, benzothiophenyl, quinolinyl, furyl, imidazolyl, indazolyl, indolyl, isoquinolinyl, oxazolyl, pyridazinyl, pyridyl, pyrimidyl, pyrrolyl, thiazolyl, thienyl, pyrazolyl, isoxazolyl, pyrazinyl, quinolyl or tetrazolyl.

Aralkyl stands for aralkyl groups that can contain up to 14 carbon atoms, preferably 6-10 carbon atoms, in the ring, and 1-8, preferably 1-4, carbon atoms in the alkyl chain. Aralkyl residues that may be considered are for example benzyl, phenylethyl, naphthylmethyl, naphthylethyl, furylmethyl, thienylethyl, pyridylpropyl. The rings can be substituted one or more times with halogen, OH, O-alkyl, $CO_2H$, $CO_2$-alkyl, $NH_2$, $NH(C_1$-$C_{10}$-alkyl), $N(C_1$-$C_{10}$-alkyl)$_2$, $NO_2$, $N_3$, CN, $C_1$-$C_{20}$-alkyl, $C_1$-$C_{10}$-perfluoro-alkyl, $C_1$-$C_{20}$-acyl, $C_1$-$C_{20}$-acyloxy groups.

When residues in the compounds according to the invention are substituted, unless otherwise specified, the residues can be substituted one or more times. Within the scope of the present invention, for all residues that occur more than once, their meaning is independent of one another. A substitution with one, two or three identical or different substituents is preferred. Substitution with one substituent is quite especially preferred.

Compounds of formula (I) are preferred,

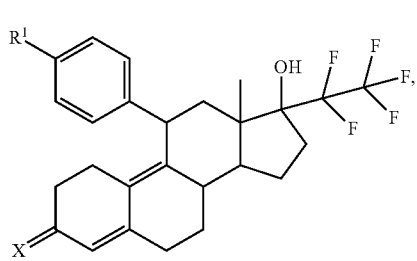

in which $R^1$ stands either for a residue Y or for a phenyl ring substituted once with a residue Y and Y is selected from the group comprising SR², S(O)R³, S(O)₂R³, S(O)(NH)R³, S(O)(NR⁴)R³, S(O)₂NR⁹R¹⁰ and R² stands for $C_1$-$C_6$-alkyl, hydrogen or $C_7$-$C_8$-aralkyl, especially preferably hydrogen, methyl, ethyl or benzyl, R³ stands for $C_1$-$C_6$-alkyl, preferably methyl or ethyl, R⁴ stands for a group $S(O)_2R^6$ and X represents oxygen, R⁶ represents phenyl or 4-methylphenyl and R⁹, R¹⁰ independently of one another represent hydrogen or $C_1$-$C_6$-alkyl or phenyl and their salts, solvates or solvates of the salts.

Compounds of formula I are especially preferred in which R¹: $S(O)_2R^3$, X: O and R³: $C_1$-$C_6$-alkyl, in particular those in which R³ denotes methyl.

Compounds of formula I are also especially preferred in which R¹: $S(O)(NH)R^3$, X: O and R³: $C_1$-$C_6$-alkyl, in particular those in which R³ denotes methyl. The preferred residue R¹ can be both in the R— and in the S-configuration, and in any mixture ratio.

The following compounds are also preferred:

(11β,17β)-17-Hydroxy-11-[4-(methylsulphanyl)phenyl]-17-(pentafluoroethyl)estra-4,9-dien-3-one (Ex. 1)

(11β,17β)-11-[4-(Ethylsulphanyl)phenyl]-17-hydroxy-17-(pentafluoroethyl)estra-4,9-dien-3-one (Ex. 2)

(11β,17β)-17-Hydroxy-11-{4-[(RS)-methylsulphinyl]phenyl}-17-(pentafluoroethyl)estra-4,9-dien-3-one (Ex. 3)

(11β,17β)-17-Hydroxy-11-[4-(methylsulphonyl)phenyl]-17-(pentafluoroethyl)estra-4,9-dien-3-one (Ex. 4)

(11β,17β)-11-[4-(Ethylsulphonyl)phenyl]-17-hydroxy-17-(pentafluoroethyl)estra-4,9-dien-3-one (Ex. 5)

(11β,17β)-11-[4-(Benzylsulphanyl)phenyl]-17-hydroxy-17-(pentafluoroethyl)estra-4,9-dien-3-one (Ex. 6)

N-[{4-[(11β,17β))-17-Hydroxy-3-oxo-17-(pentafluoroethyl)estra-4,9-dien-11-yl]phenyl}(RS)(methyl) oxido-$\lambda^6$-sulphanylidene]-4-methylbenzene sulphonamide (Ex. 7)

(11β,17β)-17-Hydroxy-11-[4-(RS-methylsulphonimidoyl)phenyl]-17-(pentafluoroethyl)estra-4,9-dien-3-one (Ex. 8)

(11β,17β)-17-Hydroxy-11-[4'-(methylsulphanyl)biphenyl-4-yl]-17-(pentafluoroethyl)estra-4,9-dien-3-one (Ex. 9)

(11β,17β)-17-Hydroxy-11-[4'-(methylsulphonyl)biphenyl-4-yl]-17-(pentafluoroethyl)estra-4,9-dien-3-one (Ex. 10)

N-[{4'-[(11β,17β)-17-Hydroxy-3-oxo-17-(pentafluoroethyl)estra-4,9-dien-11-yl]biphenyl-4-yl}(RS)(methyl) oxido-$\lambda^6$-sulphanylidene]-4-methylbenzene sulphonamide (Ex. 11)

(11β,17β)-17-Hydroxy-11-[4'-(RS-methylsulphonimidoyl)biphenyl-4-yl]-17-(pentafluoroethyl)estra-4,9-dien-3-one (Ex. 12)

(11β,17β)-17-Hydroxy-17-(pentafluoroethyl)-114-sulphanylbiphenyl-4-yl)estra-4,9-dien-3-one (Ex. 13)

4'-[(11β,17β)-17-Hydroxy-3-oxo-17-(pentafluoroethyl)estra-4,9-dien-11-yl]-N,N-dimethylbiphenyl-4-sulphonamide (Ex. 14)

4-[(11β,17β)-17-Hydroxy-3-oxo-17-(pentafluoroethyl)estra-4,9-dien-11-yl]-N,N-dimethylbenzene sulphonamide (Ex. 15)

The individually stated definitions of residues in the respective combinations or preferred combinations of residues are also replaced with any definitions of residues of some other combination independently of the respective stated combinations of the residues.

Combinations of two or more of the aforementioned preferred ranges are quite especially preferred. It was found that the compounds according to the invention and/or derivatives display good progesterone-antagonizing action.

It was found in several clinical studies that treatment with progesterone receptor antagonists (mifepristone, asoprisnil, Proellex) can lead to significant shrinking of fibroids of the uterus and a significant reduction of the symptoms associated with said fibroids of the uterus. Moreover, it was shown in clinical studies that during treatment with the stated progesterone receptor antagonists, the symptoms caused by endometriosis (especially pains) can also be reduced considerably.

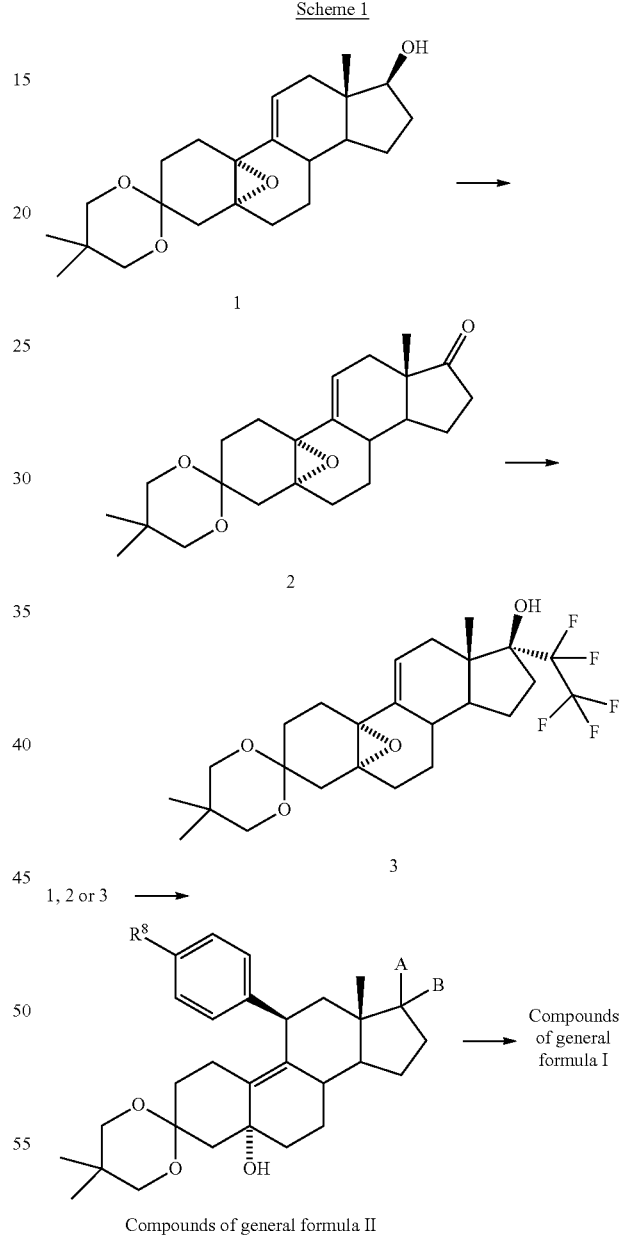

(In the above formula, A and B have the following meaning: =O; —OH/—H or —OH/—C₂F₅)

An outline of the production of compounds of general formula I is shown in Scheme 1.

The compounds with the general chemical formula are prepared starting from (5'R,8'S,10'R,13'S,14'S,17'S)-5,5,13'-trimethyl-1',2',7',8',12', 13', 14', 15', 16', 17'-decahydro- 6'H-spiro[1,3-dioxane-2,3'-[5,10]epoxycyclopenta[a]phenanthren]-17'-ol (for production see *Tetrahedron Lett.* 26, 2069-2072 (1985) by analogy with the method described in WO 98/34947 and in WO 2008/058767. After oxidation of the hydroxyl group in position 17 of the steroid backbone, introduction of the 17α-pentafluoroethyl side chain on the corresponding 17-keto compounds takes place according to the methods described in WO 98/34947 and in WO 2008/058767. Introduction of the 11β-phenyl substituents takes place by conjugated addition of arylgrignard or aryllithium reagents under copper catalysis. Compounds of general formula II are obtained, in which $R^8$ can have all meanings already stated for $R^1$ and additionally can be a hydroxy, $C_1$-$C_{10}$-alkoxy, benzyloxy, $C_1$-$C_{10}$-alkanoyloxy, benzoyloxy, silyloxyl, alkoxyalkyloxy group a Cl, Br, I or a group $C_mF_{m+1}SO_3$ with m=1-4 and A and/or B stand either for a carbonyl group or for a 17β-OH/17α-H group or for a 17β-OH/17α-C2F5 group. From compounds of general formula II it is then possible to obtain the compounds of general formula I. For this, functional groups are optionally further modified. We may mention in particular the oxidation of sulphides to sulphoxides or sulphones by methods known by a person skilled in the art and the formation of the sulphoximines from sulphides by adding CHLORAMINE-T-TRIHYDRATE® (N-Chloro-p-toluenesulfonamide sodium salt hydrate) and subsequent oxidation to the corresponding protected sulphoximine, which is then liberated e.g. by acid cleavage. As an alternative, however, it is also possible to use methods known by a person skilled in the art starting from corresponding sulphoxides. For compounds in which there is a biphenyl residue in position 11β of the steroid backbone, this can take place either directly by conjugated addition of the diarylgrignard or diaryllithium reagent under copper catalysis or alternatively e.g. by palladium-catalysed coupling reactions on the corresponding functionalized 11β-phenyl derivatives, e.g. phenyl triflate or phenyl nonaflate. Generally, both the 11β-phenyl residue and the 17β-pentafluoroethyl side chain can be introduced first. Functional groups, especially the 3-keto group, are optionally protected in the meantime, e.g. as ketal. As ketal protecting groups, we may for example mention the ethylenedioxy or 2,2-dimethylpropylene-1,2-dioxy 5 group. Hydroxyl groups are for example protected in the form of methoxymethyl, methoxyethyl, tetrahydropyranyl, benzyl, or silyl ethers.

At a suitable stage, the protecting groups are then split off by methods known by a person skilled in the art. During cleavage of the 3-ketal to the 3-keto group of the steroid backbone, a 5α-hydroxyl group optionally still present is eliminated, so that compounds of general formula 1 are formed.

Unless the production of the starting compounds is described here, these are known by a person skilled in the art or can be produced analogously to known compounds or methods described here. The mixtures of isomers can be separated into the individual compounds by usual methods, for example crystallization, chromatography or salt formation.

The production of the salts takes place in the usual way, by adding the equivalent amount or an excess of a base or acid, which is optionally in solution, to a solution of the compound with the general chemical formula I, optionally separating the precipitate or processing the solution in the usual way.

The resulting compounds of formula (I) are optionally converted, with the corresponding (i) solvents and/or (ii) bases or acids to their solvates, salts and/or solvates of the salts.

The general definitions of residues given above or stated in preferred ranges apply both to the end products of formula (I) and correspondingly also to the starting substances or intermediates needed in each case for production.

The compounds according to the invention display an unforeseeable, valuable pharmacological, pharmacokinetic and pharmacodynamic profile of action.

They are therefore suitable for use as medicinal products for the treatment and/or prophylaxis of diseases in humans and animals.

The pharmaceutical efficacy of the compounds according to the invention can be explained by their action as progesterone receptor antagonists, and thus by their antagonizing action on the progesterone receptor. Another object of the present invention is the use of the compounds according to the invention for the treatment and/or prophylaxis of diseases based on hormone-dependent hyperproliferative processes, preferably of gynaecological diseases, in particular of fibroids of the uterus, endometriosis or hormone-dependent breast cancers.

Another object of the present invention is the use of the compounds according to the invention for the treatment and/or prophylaxis of diseases, in particular the aforementioned diseases.

Another object of the present invention comprises the compounds according to the invention for use in a method of treatment and/or prophylaxis of fibroids of the uterus, endometriosis and hormone-dependent breast cancers.

Another object of the present invention is the use of the compounds according to the invention for the production of a medicinal product for the treatment and/or prophylaxis of diseases, in particular the aforementioned diseases.

Another object of the present invention is a method of treatment and/or prophylaxis of diseases, in particular the aforementioned diseases, using 0.1-100 mg of the compounds according to the invention per day per patient in the treatment of fibroids of the uterus or endometriosis and for contraceptive use or of 0.1-500 mg of the compounds according to the invention per day per patient in tumour diseases (e.g. meningioma or hormone-dependent tumours, e.g. breast cancer) and for emergency contraception. Another object of the present invention comprises medicinal products containing at least one compound according to the invention and at least one or more other active substances, in particular for the treatment and/or prophylaxis of the aforementioned diseases.

For the treatment of tumour diseases, for example the following active substances/classes of active substances can be administered either simultaneously or sequentially: SERMs, SERDs, anti-oestrogens, aromatase inhibitors, kinase inhibitors, angiogenesis inhibitors and/or cytostatics.

For the treatment of fibroids of the uterus or endometriosis, the compounds according to the invention can be combined simultaneously or sequentially with gestagens or combinations of oestrogens and gestagens. Progesterone receptor antagonists/gestagen regimens are disclosed in WO 96/15794 (Spicer et al., Balance Pharm. Inc.), WO 96/03130 (Stockemann et al., Schering AG) and PCT/EP2009/003249 (Möller et al., Bayer Schering Pharma AG). Regimens—optionally repeated—in which the progesterone receptor antagonist is administered over a period of two to four months, followed by the administration of the gestagen for a period of one to four weeks, are very suitable for the treatment of fibroids of the uterus and endometriosis. Administration of the progesterone receptor antagonist for 84 days, followed by administration of the gestagen for 14 days—optionally repeated—is especially suitable.

Simultaneous or sequential administration of the compounds according to the invention e.g. with SERMs, SERDs and oestrogens can be considered for the treatment of complaints associated with the menopause.

SERMs (selective estrogen receptor modulators) are compounds that are tissue selective and have either an anti-oestrogenic or oestrogenic action, for example on the uterus they inhibit the action of oestrogen, but on bone they have a neutral or oestrogen-like action. Examples are clomifene, raloxifene, tamoxifen, torimifene, bazedoxifene, lasofoxifene and ormeloxifene.

Selective estrogen receptor destabilizers (SERD) are pharmaceuticals which completely antagonize the oestrogen receptor ('pure anti-oestrogens' without oestrogenic active component) and lead to down-regulation of the receptor (for example fulvestrant, ZK-703 and ZK-253 (Hoffmann J et al., J Natl Cancer Inst 2004, 96:210-218) and compounds described in WO 98/007740, WO 99/33855 and WO 03/045972. Anti-oestrogens are compounds that completely antagonize the oestrogen receptor, for example fulvestrant.

Aromatase inhibitors inhibit the enzyme aromatase and therefore the aromatization of androgens to oestrogens. These include, among others, anastrozole, letrozole, exemestane, vorozole, formestans and fadrozole.

Kinase inhibitors are enzymes that transfer a phosphate residue from ATP to other substrates, and in particular to hydroxyl groups there, e.g. sorafenib (Nexavar) or imatinib (Gleevec).

Angiogenesis inhibitors, e.g. Avastin, reduce or block the supply of vessels and therefore the blood supply to a tumour.

Cytostatics, e.g. cisplatin, taxol, Taxotere are natural or synthetic substances that inhibit cell growth or cell division.

Gestagens are, in the sense of the present invention, either the natural progesterone itself or synthetic derivatives, which like progesterone itself bind to the progesterone receptor and, at dosages above the ovulation inhibiting dose, inhibit ovulation. As examples of the synthetic derivatives, we may mention drospirenone, gestodene, levonorgestrel, cyproterone acetate, desogestrel and 3-ketodesogestrel, norethisterone, norethisterone acetate and dienogest.

Combinations of gestagens and oestrogens are the combinations of active substances that are contained in the oral contraceptives that are known per se, for example Yasmin, Femovan, Triquilar, Marvelon, YAZ etc.

The compounds according to the invention can act systemically and/or locally. For this purpose they can be applied in a suitable way, e.g. by the oral, intrauterine, intravaginal, parenteral, pulmonary, nasal, sublingual, lingual, buccal, rectal, dermal, transdermal, conjunctival, or otic route or as an implant or stent. Intrauterine means in particular application by means of an IUS (intrauterine system) or IUD (intrauterine device). Intravaginal application can be effected by means of, among others, IVRNRS (intravaginal ring/vaginal ring system).

Forms for intrauterine or intravaginal application (cf. e.g. WO 01/47490, especially page 1, line 10 to line 5, line 13 and line 7, line 19 to line 58, line 6, or for vaginal rings: WO 06/010097, especially page 10, line 22 to page 14, line 28) can contain the compounds according to the invention and non-silicone and/or silicone polymers, in particular also siloxane-based elastomers (cf. WO 01/47490, especially page 7, line 19-page 15, line 15).

For these routes of administration, the compounds according to the invention can be administered in suitable dosage forms.

Quick-release and/or modified-release dosage forms functioning according to the prior art are suitable for oral administration, containing the compounds according to the invention in crystalline and/or amorphous and/or dissolved form, e.g. tablets (uncoated or coated tablets, for example with enteric coatings or delayed-dissolving or insoluble coatings, which control the release of the compound according to the invention), tablets or films/wafers that quickly disintegrate in the oral cavity, films/lyophilizates, capsules (for example hard-gelatin or soft-gelatin capsules), coated tablets, granules, pellets, powders, emulsions, suspensions, aerosols or solutions.

Parenteral application can take place while avoiding an absorption step (e.g. intravenous, intraarterial, intracardial, intraspinal or intralumbar) or with inclusion of absorption (e.g. intramuscular, subcutaneous, intradermal, percutaneous or intraperitoneal). Injection and infusion preparations in the form of solutions, suspensions, emulsions, lyophilizates or sterile powders, among others, are suitable as dosage forms for parenteral administration.

For the other routes of administration, the following are suitable, e.g. inhalation dosage forms (including powder inhalers, nebulizers), nasal drops, solutions, and sprays; tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (for example patches), milk, pastes, foams, dusting powders, implants or stents. The compounds according to the invention can be converted to the aforementioned dosage forms. This can be carried out in a manner that is known per se, by mixing with inert, non-toxic, pharmaceutically suitable excipients. These excipients include, among others, carrier substances (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colouring matter (e.g. inorganic pigments, for example iron oxides) and taste and/or odour correctants.

Another object of the present invention comprises medicinal products that contain at least one compound according to the invention, usually together with one or more inert, non-toxic, pharmaceutically suitable excipients, and use thereof for the aforementioned purposes.

Nevertheless, it may optionally be necessary to deviate from the stated amounts, namely depending on body weight, route of administration, individual response to the active substance, type of preparation and point of time or interval when application takes place. Thus, in some cases it may be sufficient to use less than the aforementioned minimum amount, whereas in other cases the stated upper limit must be exceeded. In the case of the administration of larger amounts it may be advisable to distribute these in several individual doses throughout the day.

The percentages in the following tests and examples are, unless stated otherwise, percentages by weight; parts are parts by weight. Proportions of solvents, dilution ratios and concentration figures for liquid/liquid solutions always refer to volume.

The following examples serve to explain the invention without limiting it in any way.

EXAMPLE 1

(11β,17β)-17-hydroxy-11-[4-(methylsulphanyl)phenyl]-17-(pentafluoroethyl)estra-4,9-dien-3-one

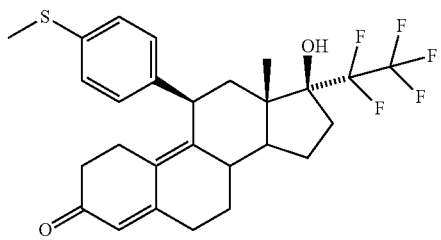 [SMILES: CSc1ccc([C@H]2C[C@@]3(C)C(CC[C@@]3(O)C(F)(F)C(F)(F)F)C3CCC4=CC(=O)CCC4=C32)cc1]

a) (5'R,8'S,10'R,13'S,14'S,17'S)-5,5,13'-trimethyl-17'-(pentafluoroethyl)-1',2',7',8',12',13',14',15',16',17'-decahydro-6'H-spiro[1,3-dioxane-2,3'-[5,10]epoxycyclopenta[a]phenanthrene]-17'-ol

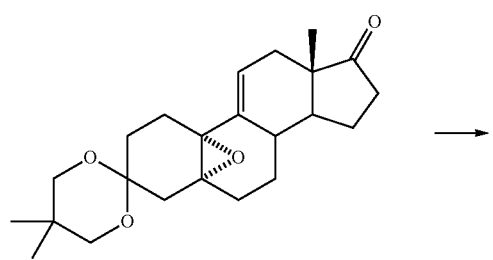

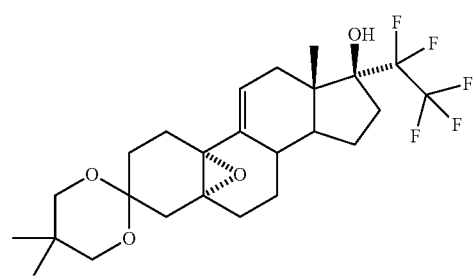

50 g of (5'R,8'S,10'R,13'S,14'S)-5,5,13'-trimethyl-1',2',6',7',8',12',13',14',15',16'-decahydro-17'H-spiro[1,3-dioxane-2,3'-[5,10]epoxycyclopenta[a]phenanthren]-17-one (for preparation see *Tetrahedron Lett.* 26, 2069-2072 (1985) was added to 116 g of condensed pentafluoroiodoethane in 500 ml absolute toluene at −70° C. 290 ml of a 1.5-molar solution of methyllithium-lithium bromide complex in diethyl ether was added to this at the same temperature. It was then stirred for one hour at 0° C. The reaction mixture was then added to saturated aqueous ammonium chloride solution and was extracted with ethyl acetate. The organic phase was washed with saturated aqueous sodium chloride solution, dried over sodium sulphate and concentrated under vacuum. The raw product was dissolved in 200 ml acetone and 450 ml water was added. The precipitated product was filtered off and dried in vacuum.

Yield 61.6 g

1H-NMR (400 MHz, CDCl3): δ=6.04 brd (1H); 3.60 d (1H); 3.35-3.50 m (3H); 2.51 dbr (1H); 1.06 s (3H); 0.93 s (3H); 0.85 s (3H).

b) (5R,8S,11R,13S,14S,17S)-5,5',13-trimethyl-11-[4-(methylsulphanyl)phenyl]-17-(pentafluoroethyl)-1,2,6,7,8,11,12,13,14,15,16,17-dodecahydrospiro[cyclopenta[a]phenanthrene-3,2'-[1,3]dioxane]-5,17(4H)-diol

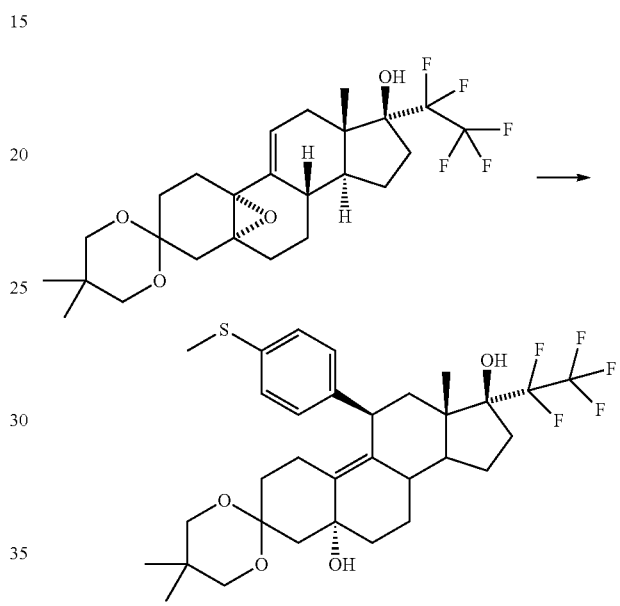

1.23 g magnesium shavings were suspended in 5 ml THF and 50 μl dibromoethane was added, while stirring. A solution of 10.31 g of 1-bromo-4-(methylthiopheny)benzene in 60 ml THF was added to the suspension in such a way that the reaction temperature did not go above 55° C. Then it was stirred for a further hour. The resultant solution was then cooled to 0° C. 151 mg CuCl was added and it was stirred for a further 15 minutes at 0° C. Then a solution of 5 g of the substance described in example 1a) in 50 ml THF was added. Then the reaction mixture was allowed to reach 23° C. in the space of approx. 3 hours, with stirring, and then it was stirred at this temperature for a further 10 hours. Then saturated aqueous NH$_4$Cl solution was added to the reaction mixture, with external cooling. Stirring was continued for 30 minutes and it was then extracted several times with ethyl acetate. The combined organic phases were washed with saturated sodium chloride solution and dried over sodium sulphate. The raw product was purified by silica gel chromatography followed by crystallization from a mixture of dichloromethane and diisopropyl ether. This gave 5.72 g of the title compound.

$^1$H-NMR (300 MHz, CDCl$_3$): δ=7.50 d (2H); 7.30 d (2H); 4.41 s (1H); 4.28 dbr (1H); 3.40-3.60 m (4H); 2.51 s (3H); 1.05 s (3H); 0.87 s (3H); 0.53 s (3H).

c) (11β,17β)-17-hydroxy-11-[4-(methylsulphanyl)phenyl]-17-(pentafluoroethyl)estra-4,9-dien-3-one a) (5R,8S,11R,13S,14S,17S)-11-[4-(ethylsulphanyl)phenyl]-5',5',13-trimethyl-17-(pentafluoroethyl)-1,2,6,7,8,11,12,13,14,15,16,17-dodecahydrospiro[cyclopenta[a]phenanthrene-3,2'-[1,3]dioxane]-5,17(4H)-diol

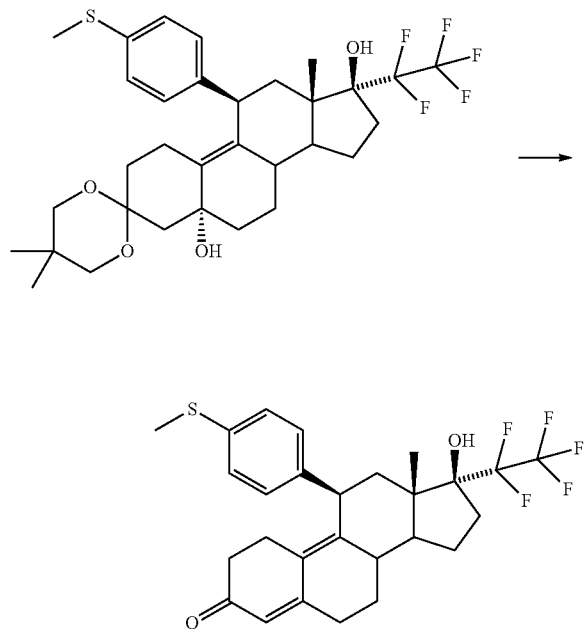

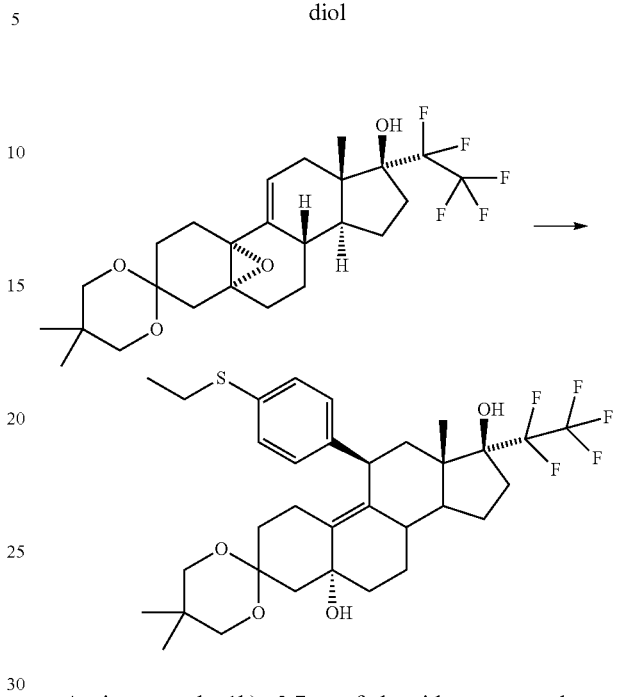

As in example 1b), 2.7 g of the title compound was prepared from 3 g of the compound described in 1a), 888 mg magnesium shavings, 91 mg CuCl and 7.94 g of 1-bromo-4-(ethylthiopheny)benzene in THF.

$^1$H-NMR (300 MHz, CDCl$_3$): δ=7.50 d (2H); 7.38 d (2H); 4.43 s (1H); 4.39 dbr (1H); 3.40-3.60 m (3H); 2.95 q (2H); 1.30 t (3H); 1.07 s (3H); 0.87 s (3H); 0.53 s (3H).

b) (11β,17β)-11-[4-(ethylsulphanyl)phenyl]-17-hydroxy-17-(pentafluoroethyl)estra-4,9-dien-3-one 500 mg of the compound described in 1b) was dissolved in 15 ml methanol. 360 μl of semi-concentrated sulphuric acid was added and stirring was continued for 3 hours at 23° C. Then the reaction mixture was poured into saturated aqueous sodium hydrogen carbonate solution. It was extracted several times with ethyl acetate. The combined organic phases were washed with saturated aqueous sodium chloride solution, dried over sodium sulphate and concentrated under vacuum. The raw product was purified by silica gel chromatography. This gave 297 mg of the title compound.

$^1$H-NMR (300 MHz, CDCl$_3$): δ=7.20 d (2H); 7.13 d (2H); 5.80 sbr (1H); 4.45 dbr (1H); 2.51 s (3H); 0.68 s (3H).

EXAMPLE 2

(11β,17β)-11-[4-(ethylsulphanyl)phenyl]-17-hydroxy-17-(pentafluoroethyl)estra-4,9-dien-3-one

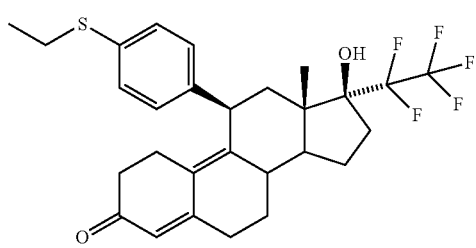 [SMILES: CCSc1ccc([C@H]2C[C@@]3(C)C(CC[C@@]3(O)C(F)(F)C(F)(F)F)C3CCC4=CC(=O)CCC4=C32)cc1]

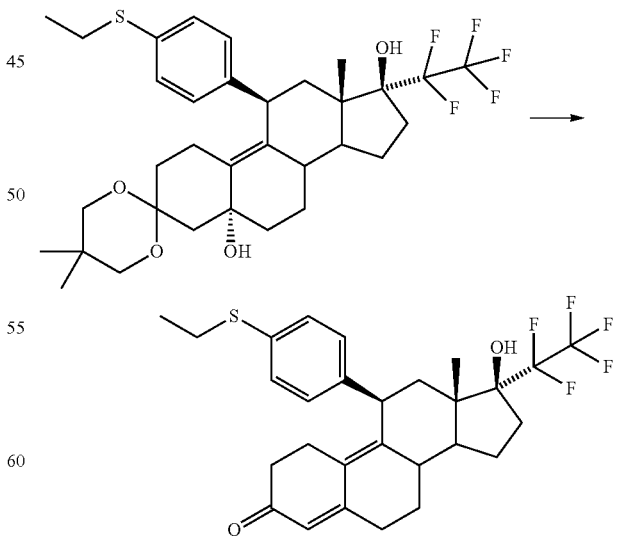

As in example 1c), 125 mg of the title compound was prepared from 200 mg of the compound prepared in 2a) by reaction with semi-concentrated sulphuric acid in methanol.

$^1$H-NMR (300 MHz, CDCl$_3$): δ=7.21 d (2H); 7.08 d (2H); 5.78 sbr (1H); 4.43 dbr (1H); 2.93 q (2H); 1.29 t (3H); 0.60 s (3H).

EXAMPLE 3

(11β,17β)-17-Hydroxy-11-{4-[(RS)-methylsulphinyl]phenyl}-17-(pentafluoroethyl)estra-4,9-dien-3-one

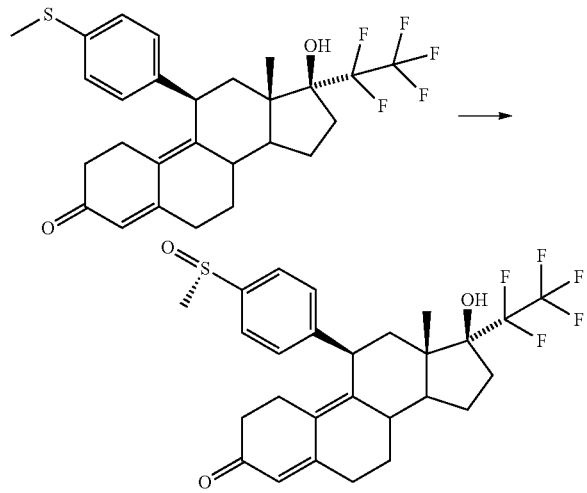

180 μl of 30% hydrogen peroxide solution was added to 0.5 ml of trifluoroacetic acid at 23° C. It was stirred for 30 minutes and then the mixture was added to a suspension, cooled to 10° C., of 533 mg of the compound prepared in example 1c), in 1.8 ml of trifluoroacetic acid. It was stirred for a further 2 hours at 10° C. Then the reaction mixture was poured into ice water. It was stirred for a further 2 hours and then the precipitated product was filtered off. The raw product obtained was purified by silica gel chromatography. This gave 146 mg of the title compound and 123 mg of the compound described in example 4.

$^1$H-NMR (400 MHz, CDCl$_3$): δ=7.58 d (2H); 7.38 d (2H); 5.80 sbr (1H); 4.50 dbr (1H); 2.71 s (3H); 0.58 s (3H)+0.56 s (3H) (mixture of the diastereomers).

EXAMPLE 4

(11β,17β)-17-Hydroxy-11-[4-(methylsulphonyl)phenyl]-17-(pentafluoroethyl)estra-4,9-dien-3-one

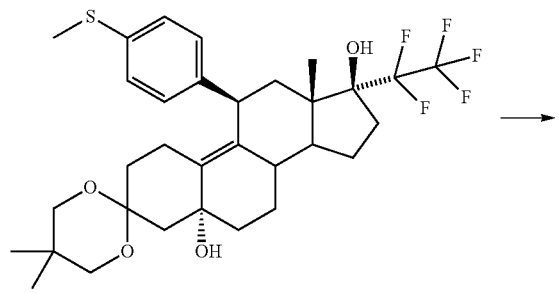

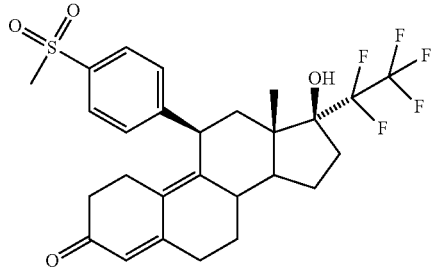

5 g of the compound described in example 1 b) was dissolved in a mixture of 140 ml THF and 140 ml methanol. A solution of 20 g OXONE® (monopersulfate compound) in 94 ml water was slowly added dropwise at 0° C. Then it was stirred for a further 3.5 hours at 0° C. Then a mixture of water and dichloromethane was added to the reaction mixture. The phases were separated and the aqueous phase was extracted several times with dichloromethane. The combined organic phases were washed with saturated aqueous sodium chloride solution, dried over sodium sulphate and concentrated under vacuum. The raw product was purified by silica gel chromatography. This gave 3.8 g of the title compound.

$^1$H-NMR (300 MHz, CDCl$_3$): δ=7.86 d (2H); 7.40 d (2H); 5.81 sbr (1H); 4.50 dbr (1H); 3.07 s (3H); 0.51 s (3H).

EXAMPLE 5

(11β,17β)-11-[4-(ethylsulphonyl)phenyl]-17-hydroxy-17-(pentafluoroethyl)estra-4,9-dien-3-one

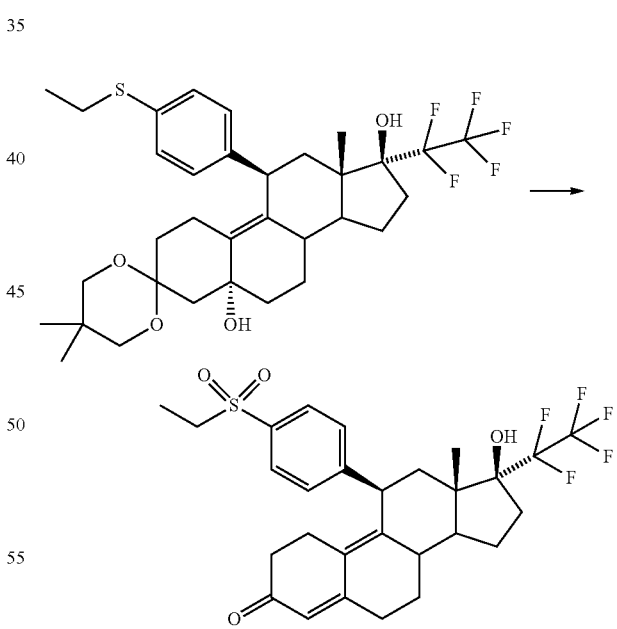

As in example 4), after purification by silica gel chromatography, 183 mg of the title compound was obtained by reaction of 400 mg of the compound described in example 2a) with 1.56 g OXONE® (monopersulfate compound) in a mixture of 10 ml THF and 10 ml methanol.

$^1$H-NMR (400 MHz, CDCl$_3$): δ=7.82 d (2H); 7.40 d (2H); 5.80 sbr (1H); 4.52 dbr (1H); 3.13 q (2H); 1.28 t (3H); 0.51 s (3H).

EXAMPLE 6

(11β,17β)-11-[4-(benzylsulphanyl)phenyl]-17-hydroxy-17-(pentafluoroethyl)estra-4,9-dien-3-one

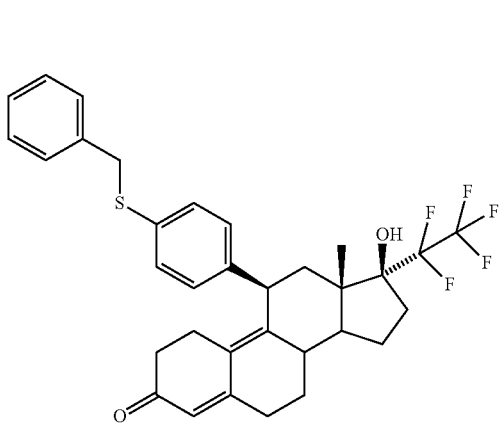 [SMILES: C[C@]12C[C@H](c3ccc(SCc4ccccc4)cc3)C3=C4CCC(=O)C=C4CCC3C1CC[C@@]2(O)C(F)(F)C(F)(F)F]

a) (5R,8S,11R,13S,14S,17S)-11-[4-(benzylsulphanyl)phenyl]-5',5',13-trimethyl-17-(pentafluoroethyl)-1,2,6,7,8,11,12,13,14,15,16,17-dodecahydrospiro[cyclopenta[a]phenanthrene-3,2'-[1,3]dioxane]-5,17(4H)-diol

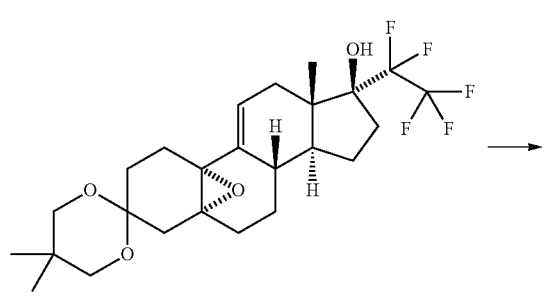

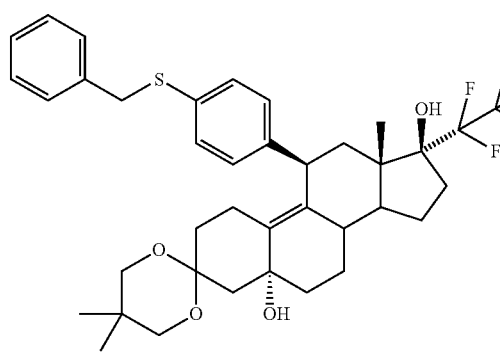

As in example 1 b), 6.65 g of the title compound was prepared from 8.5 g of the compound described in 1a), 2.64 g magnesium shavings, 171 mg CuCl and 30.36 g of 1-benzylsulphanyl-4-bromobenzene in THF.

$^1$H-NMR (300 MHz, CDCl$_3$): δ=7.13-7.30 m (7H); 7.10 d (2H); 4.44 s (1H); 4.27 dbr (1H); 4.05 s (2H); 3.40-3.60 m (4H); 1.05 s (3H); 0.87 s (3H); 0.51 s (3H).

b) (11β,17β)-11-[4-(benzylsulphanyl)phenyl]-17-hydroxy-17-(pentafluoroethyl)estra-4,9-dien-3-one

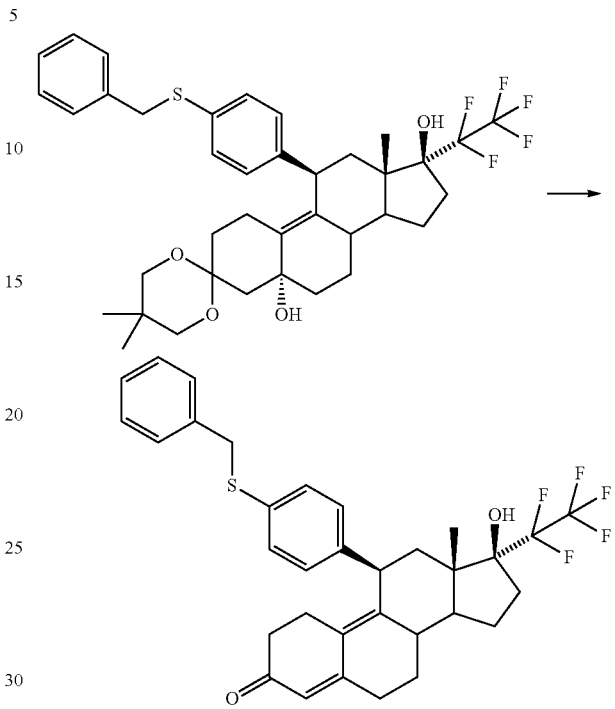

As in example 1c), 1.02 g of the title compound was prepared from 1.62 g of the compound described in example 6a) by reaction with semi-concentrated sulphuric acid in methanol.

$^1$H-NMR (300 MHz, CDCl$_3$): δ=7.15-7.40 m (7H); 7.06 d (2H); 5.78 sbr (1H); 4.40 dbr (1H); 4.08 s (2H); 0.59 s (3H).

EXAMPLE 7

N-[{4-[(11β,17β)-17-hydroxy-3-oxo-17-(pentafluoroethyl)estra-4,9-dien-11-yl]phenyl}(RS)(methyl)oxido-λ$^6$-sulphanylidene]-4-methylbenzene sulphonamide

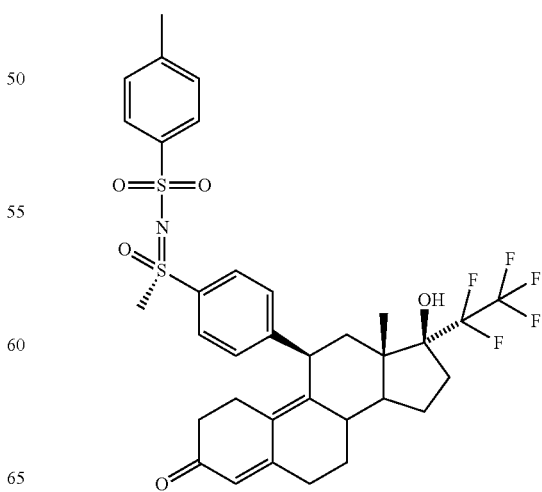

a) N-[{4-[(5R,8S,11R,13S,14S,17S)-5,17-Dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxane]-11-yl]phenyl}(RS)(methyl)-λ⁴-sulphanylidene]-4-methylbenzene sulphonamide b) N-[{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxane]-11-yl]phenyl}(RS)(methyl) oxido-λ⁶-sulphanylidene]-4-methylbenzene sulphonamide

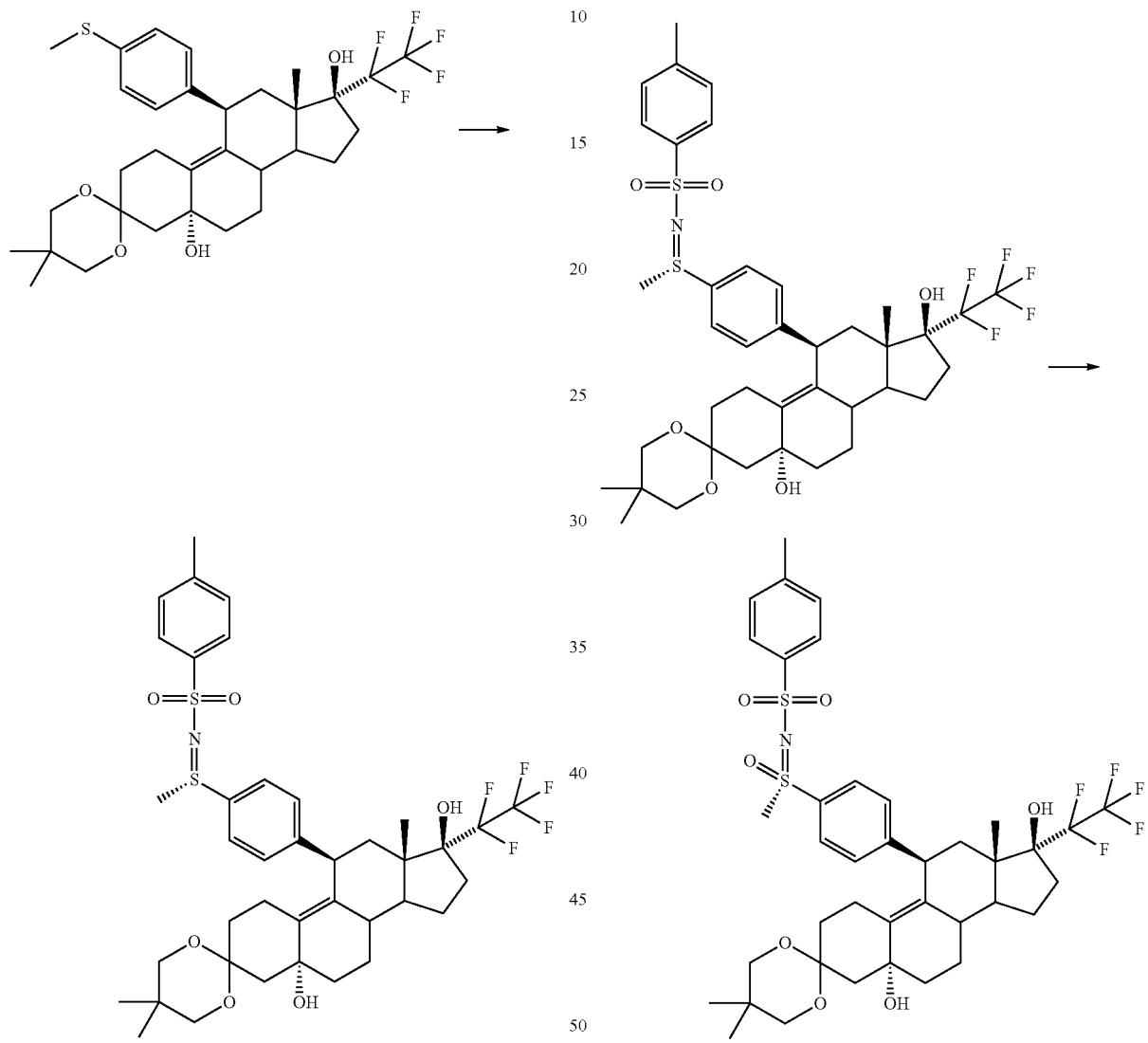

3 g of the substance described in example 1 b) was suspended in 80 ml acetonitrile. 1.64 g of Chloramine-T-Trihydrate® was added and stirring was continued for 20 hours at 23° C. Then the reaction mixture was diluted with 70 ml dichloromethane. After filtering off precipitated sodium chloride, it was concentrated in vacuum. The raw product was purified by silica gel chromatography. This gave 3.16 g of the title compound.

¹H-NMR (300 MHz, CDCl₃): δ=7.74 d (2H); 7.49 d (2H); 7.38 d (2H); 7.18 d (2H); 4.40 s (1H); 4.33 dbr (1H); 3.40-3.70 m (4H); 2.80 (3H); 2.37 s (3H), 1.05 s (3H); 0.89 s (3H); 0.45 s (3H) (mixture of diastereomers).

3.16 g of the compound obtained in 7a) was dissolved in 2.5 ml acetonitrile and 1.6 ml methanol. 1.22 g of sodium carbonate and 2.34 ml of 30% hydrogen peroxide solution were added. Then it was stirred for 2.5 hours at 23° C. The reaction mixture was then poured into water. It was extracted several times with dichloromethane. The combined organic phases were washed with saturated aqueous sodium chloride solution, dried over sodium sulphate and concentrated under vacuum. The raw product was purified by silica gel chromatography. This gave 2.56 g of the title compound.

¹H-NMR (300 MHz, CDCl₃): δ=7.78-8.00 m (4H); 7.51 d (2H); 7.31 d (2H); 4.50 s (1H); 4.44 dbr (1H); 3.45-3.67 m (7H); 2.46 s (3H); 1.09 s (3H); 0.91 s (3H); 0.51 s (3H) (mixture of diastereomers).

c) N-[{4-[(11β,17β)-17-hydroxy-3-oxo-17-(pentafluoroethyl)estra-4,9-dien-11-yl]phenyl}(RS)(methyl) oxido-λ⁶-sulphanylidene]-4-methylbenzene sulphonamide

EXAMPLE 8

(11β,17β)-17-Hydroxy-11-[4-(RS-methylsulphonimidoyl)phenyl]-17-(pentafluoroethyl)estra-4,9-dien-3-one

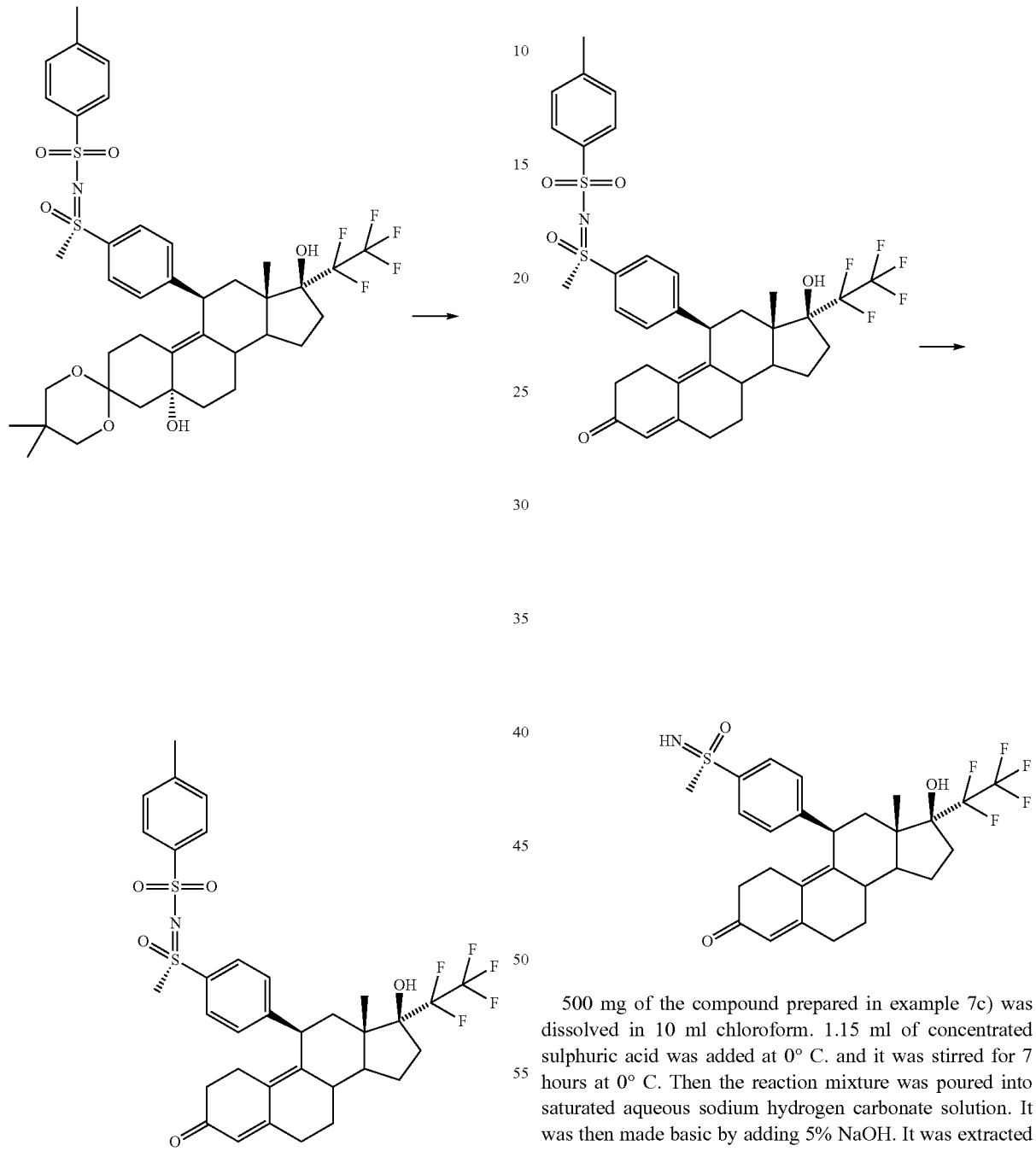

As in example 1c), 2.2 g of the title compound was prepared from 2.72 g of the compound prepared in 7b) by reaction with semi-concentrated sulphuric acid in methanol.

¹H-NMR (300 MHz, CDCl₃): δ=7.95 d (2H); 7.86 d (2H); 7.45 d (2H); 7.28 d (2H); 5.81 sbr (1H); 4.51 dbr (1H); 3.41 s (3H); 2.40 s (3H); 0.51 s (3H) (mixture of diastereomers).

500 mg of the compound prepared in example 7c) was dissolved in 10 ml chloroform. 1.15 ml of concentrated sulphuric acid was added at 0° C. and it was stirred for 7 hours at 0° C. Then the reaction mixture was poured into saturated aqueous sodium hydrogen carbonate solution. It was then made basic by adding 5% NaOH. It was extracted several times with dichloromethane. The combined organic phases were washed with saturated aqueous sodium chloride solution, dried over sodium sulphate and concentrated under vacuum. The raw product was purified by silica gel chromatography. This gave 306 mg of the title compound.

¹H-NMR (300 MHz, CDCl₃): δ=7.91 d (2H); 7.39 d (2H); 5.81 sbr (1H); 4.50 dbr (1H); 3.12 s (3H)+3.10 s (3H); 0.56 s (3H)+0.40 s (3H) (mixture of diastereomers).

EXAMPLE 9

(11β,17β)-17-Hydroxy-11-[4'-(methylsulphanyl)biphenyl-4-yl]-17-(pentafluoroethyl)estra-4,9-dien-3-one

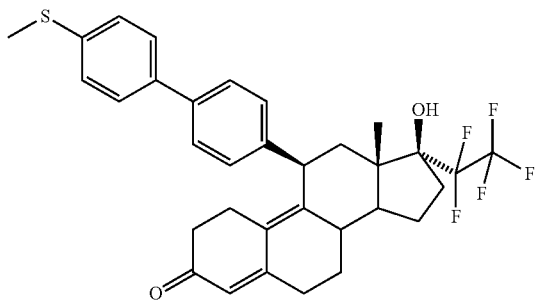 [SMILES: CSc1ccc(-c2ccc([C@H]3C[C@@]4(C)C(CC[C@@]4(O)C(F)(F)C(F)(F)F)C4CCC5=CC(=O)CCC5=C43)cc2)cc1]

a) (5R,8S,11R,13S,14S,17S)-11-[4-(benzyloxy)phenyl]-5,5,13-trimethyl-17-(pentafluoroethyl)-1,2,6,7,8,11,12,13,14,15,16,17-dodecahydrospiro[cyclopenta[a]phenanthrene-3,2'-[1,3]dioxane]-5,17(4H)-diol

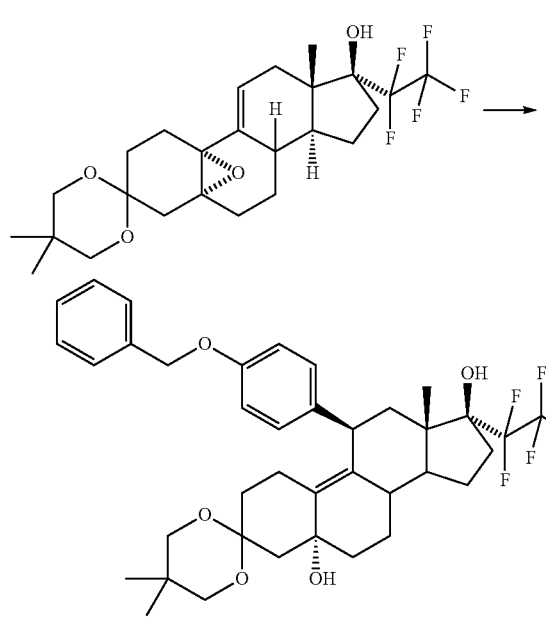

2.47 g magnesium shavings were suspended in 5 ml THF and 50 μl dibromoethane was added, while stirring. A solution of 26.7 g of 1-bromo-4-(phenylmethoxy)benzene in 115 ml THF was slowly added to the suspension at 65° C. The resultant solution was cooled to 0° C. 301 mg CuCl was added to it. It was stirred for 10 minutes at 0° C. and then a solution of 10 g of the substance described in example 1a) in 70 ml THF was added slowly. The reaction mixture was allowed to warm to 23° C. while stirring in the space of approx. 3 hours and was then stirred at this temperature for a further 10 hours. Then saturated aqueous NH₄Cl solution was added to the reaction mixture, with external cooling. It was stirred for a further 30 minutes and then extracted several times with ethyl acetate. The combined organic phases were washed with saturated sodium chloride solution and dried over sodium sulphate. The raw product was purified by silica gel chromatography followed by crystallization from a mixture of dichloromethane and diisopropyl ether. This gave 9.7 g of the title compound.

$^1$H-NMR (400 MHz, CDCl$_3$): δ=7.30-7.50 m (5H); 7.12 d (2H); 6.88 d (2H); 5.02 s (2H); 4.43 s (1H); 4.28 dbr (1H); 3.50-3.60 m (3H); 3.42 d (1H); 1.06 s (3H); 0.87 s (3H); 0.56 s (3H).

b) (5R,8S,11R,13S,14S,17S)-11-[4-(benzyloxy)phenyl]-5',5',13-trimethyl-17-(pentafluoroethyl)-1,2,6,7,8,11,12,13,14,15,16,17-dodecahydrospiro[cyclopenta[a]phenanthrene-3,2'-[1,3]dioxane]-5,17(4H)-diol

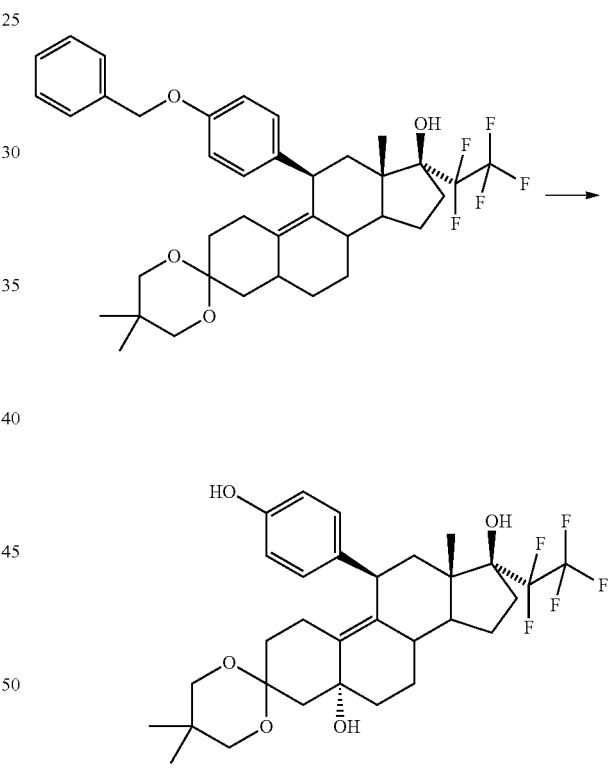

5.53 g ammonium formate and 972 mg palladium on activated charcoal (10%) were added to a solution of 9.72 g of the compound described in 9a) in 100 ml methanol. It was stirred for 2 hours at 23° C. and then filtered on CELITE® (diatomaceous earth) The filtrate was concentrated under vacuum. This gave 8.5 g of raw product, which was used in the next stage without purification.

$^1$H-NMR (300 MHz, CDCl$_3$): δ=7.05 d (2H); 6.70 d (2H); 4.43 sbr (1H); 4.27 dbr (1H); 3.50-3.58 m (3H); 3.41 sbr (1H); 1.94 s (3H); 0.86 s (3H); 0.54 s (3H).

c) 4-[(5R,8S,11R,13S,14S,17S)-5,17-Dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl]phenyl-1,1,2,2,3,3,4,4,4-nonafluorobutane-1-sulphonate d) (5R,8S,11R,13S,14S,17S)-5',5',13-trimethyl-11-[4'-(methylsulphanyl)biphenyl-4-yl]-17-(pentafluoroethyl)-1,2,6,7,8,11,12,13,14,15,16,17-dodecahydrospiro[cyclopenta[a]phenanthrene-3,2'-[1,3]dioxane]-5,17(4H)-diol

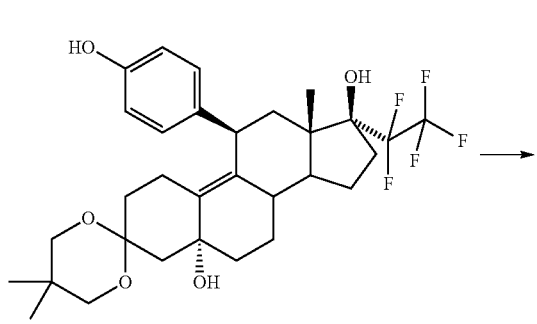

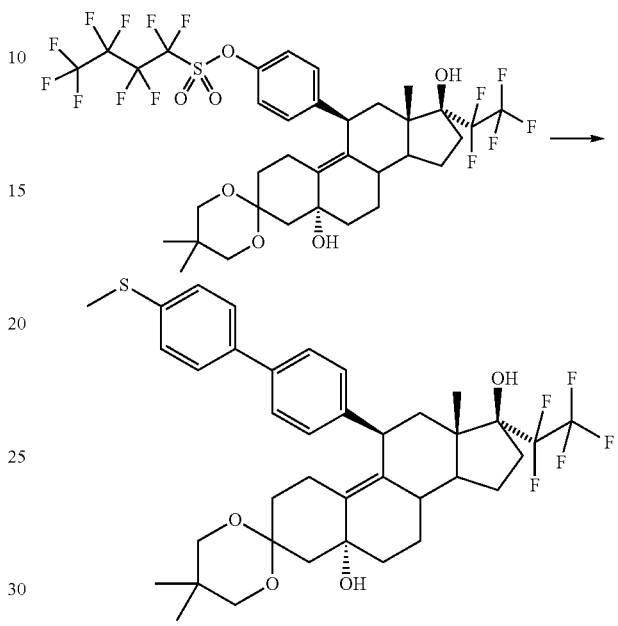

2 ml of a 2-molar aqueous sodium carbonate solution, 131 mg of lithium chloride, 240 mg of 4-(methylthio)phenylboronic acid and 192 mg of tetrakis(triphenylphosphine)palladium were added to a solution of 1.2 g of the compound described in 9c) in a mixture of 12 ml toluene and 6 ml ethanol. Then it was boiled under reflux for 2 hours. Then a mixture of ethyl acetate and water was added to the reaction mixture. It was extracted several times with ethyl acetate. The combined organic phases were washed with saturated aqueous sodium chloride solution, dried over sodium sulphate and concentrated under vacuum. The raw product was purified by silica gel chromatography. This gave 927 mg of the title compound.

$^{1}$H-NMR (300 MHz, CDCl$_{3}$): δ=7.45-7.55 m (4H); 7.30 d (2H); 7.27 d (2H); 4.45 s (1H); 4.35 dbr (1H); 3.40-3.60 m (4H); 2.50 s (3H); 1.07 s (3H); 0.97 s (3H); 0.58 s (3H).

e) (11β,17β)-17-hydroxy-11-[4'-(methylsulphanyl)biphenyl-4-yl]-17-(pentafluoroethyl)estra-4,9-dien-3-one

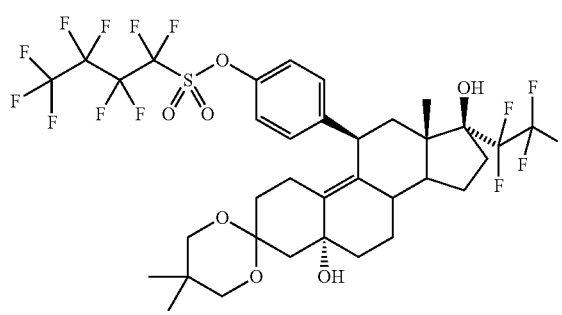

14.64 ml of a 1.6-molar solution of n-butyllithium in hexane was added at 0° C. to a solution of 9.16 g of the compound described in 9b) in 100 ml absolute THF. It was stirred for 30 minutes at 0° C. and then 5.62 ml perfluorobutane-1-sulphonyl fluoride was added slowly. Then it was stirred for a further 1.5 hours at 0° C. Then the reaction mixture was poured into a mixture of 300 ml of saturated sodium hydrogen carbonate solution and 90 ml of 2N sodium hydroxide solution. It was stirred for 45 minutes and then extracted several times with ethyl acetate. The combined organic phases were washed with saturated sodium chloride solution and dried over sodium sulphate. The raw product obtained was purified by silica gel chromatography. This gave 10.1 g of the title compound.

$^{1}$H-NMR (400 MHz, CDCl$_{3}$): δ=7.28 d (2H); 7.18 d (2H); 4.42 s (1H); 4.34 dbr (1H); 3.50-3.58 m (3H); 3.42 d (1H); 1.05 s (3H); 0.86 s (3H); 0.50 s (3H).

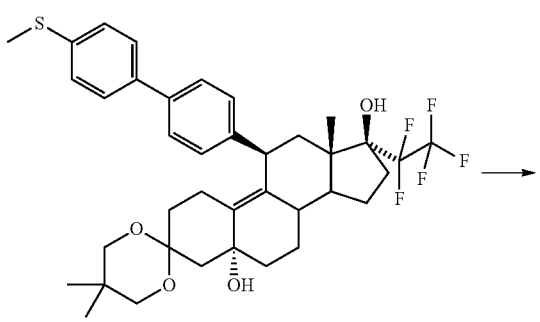

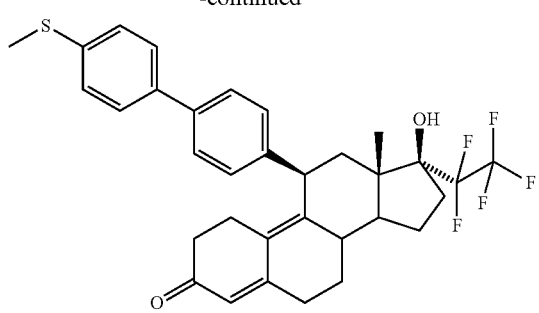

As in example 1c), 82 mg of the title compound was prepared from 120 mg of the compound prepared in 9d) by reaction with semi-concentrated sulphuric acid in methanol.

$^{1}$H-NMR (400 MHz, CDCl$_{3}$): δ=7.45-7.58 m (4H); 7.30 d (2H); 7.24 d (2H); 5.80 sbr (1H); 4.50 dbr (1H); 2.50 s (3H); 0.62 s (3H).

EXAMPLE 10

(11β,17β)-17-hydroxy-11-[4'-(methylsulphonyl)biphenyl-4-yl]-17-(pentafluoroethyl)estra-4,9-dien-3-one

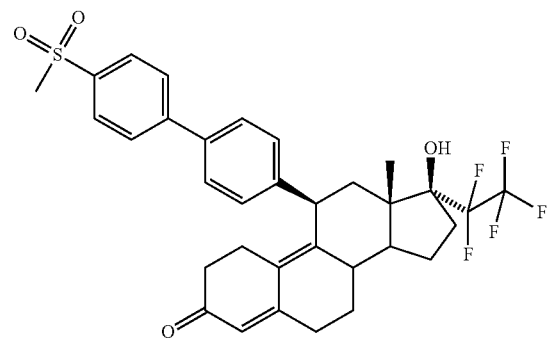 [SMILES: C[C@]12C[C@H](c3ccc(-c4ccc(S(C)(=O)=O)cc4)cc3)C3=C4CCC(=O)C=C4CCC3C1CC[C@@]2(O)C(F)(F)C(F)(F)F]

a) (5R,8S,11R,13S,14S,17S)-5',5',13-trimethyl-11-[4'-(methylsulphonyl)biphenyl-4-yl]-17-(pentafluoroethyl)-1,2,6,7,8,11,12,13,14,15,16,17-dodecahydrospiro[cyclopenta[a]phenanthrene-3,2'-[1,3]dioxane]-5,17(4H)-diol

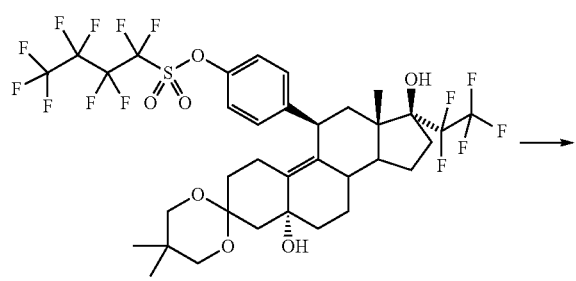

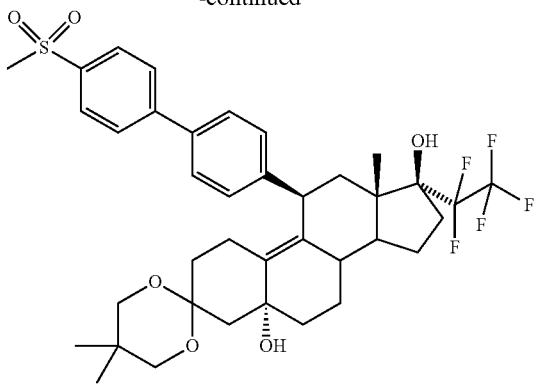

As in example 9d), 256 mg of the title compound was prepared from 500 mg of the compound described in example 9c) and (4-methylsulphonylphenyl)boronic acid in the presence of tetrakis(triphenylphosphine)palladium, lithium chloride, 2-molar aqueous sodium carbonate solution in a mixture of toluene and ethanol.

$^{1}$H-NMR (300 MHz, CDCl$_{3}$): δ=8.03 d (2H); 7.80 d (2H); 7.58 d (2H); 7.39 d (2H); 4.48 s (1H); 4.45 dbr (1H); 3.45-3.65 m (4H); 3.12 s (3H); 1.10 s (3H); 0.91 s (3H); 0.62 s (3H).

b) (11β,17β)-17-hydroxy-11-[4'-(methylsulphonyl)biphenyl-4-yl]-17-(pentafluoroethyl)estra-4,9-dien-3-one

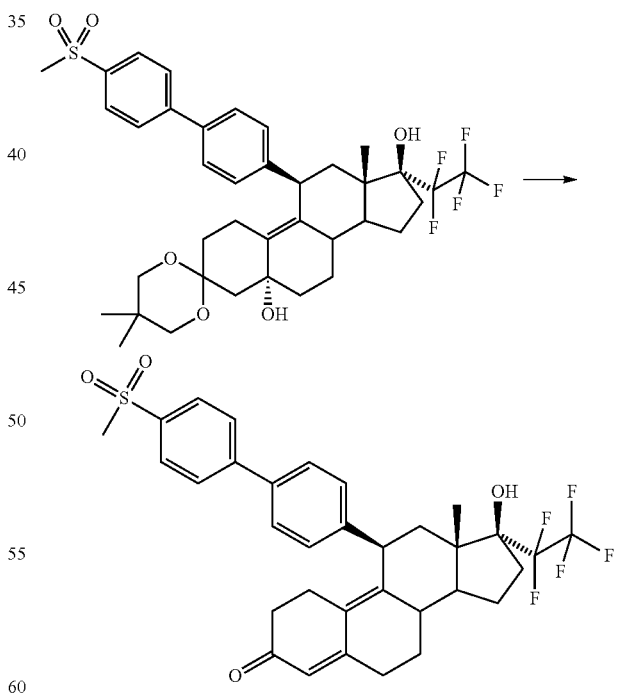

As in example 1c), 62 mg of the title compound was prepared from 110 mg of the compound prepared in 10a) by reaction with semi-concentrated sulphuric acid in methanol.

$^{1}$H-NMR (400 MHz, CDCl$_{3}$): δ=8.00 d (2H); 7.75 d (2H); 7.55 d (2H); 7.30 d (2H); 5.80 sbr (1H); 4.50 dbr (1H); 3.09 s (3H); 0.65 s (3H).

EXAMPLE 11

N-[{4'-[(11β,17β)-17-hydroxy-3-oxo-17-(pentafluoroethyl)estra-4,9-dien-11-yl]biphenyl-4-yl}(RS)(methyl) oxido-λ⁶-sulphanylidene]-4-methylbenzene sulphonamide

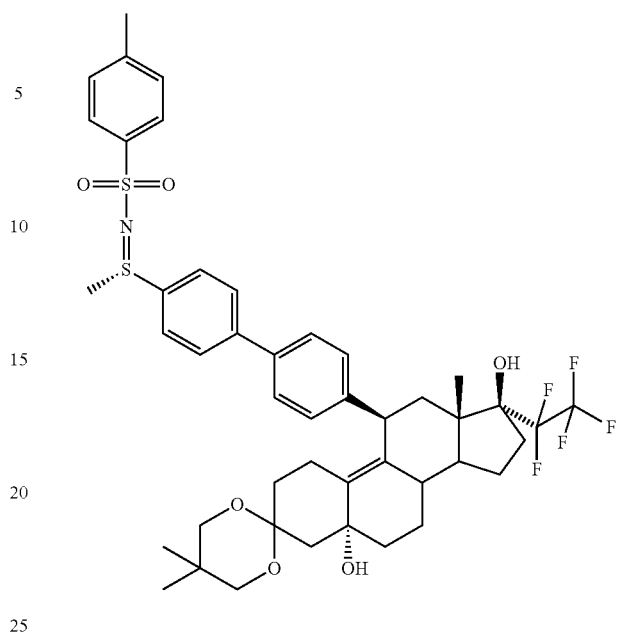

As in example 7a), 715 mg of the title compound was prepared from 800 mg of the compound prepared in example 9d) with CHLORAMINE-T-TRIHYDRATE® (N-Chloro-p-toluenesulfonamide sodium salt hydrate) in acetonitrile.

¹H-NMR (300 MHz, CDCl₃): δ=7.65-7.80 (6H); 7.47 d (2H); 7.30 d (2H); 7.18 d (2H); 4.45 s (1H); 4.39 dbr (1H); 3.40-3.60 m (4H); 2.87 (3H); 2.35 s (3H), 1.03 s (3H); 0.87 s (3H); 0.56 s (3H) (mixture of diastereomers).

b) N-[{4'-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl] biphenyl-4-yl}(RS)(methyl)oxido-λ⁶-sulphanylidene]-4-methylbenzene sulphonamide

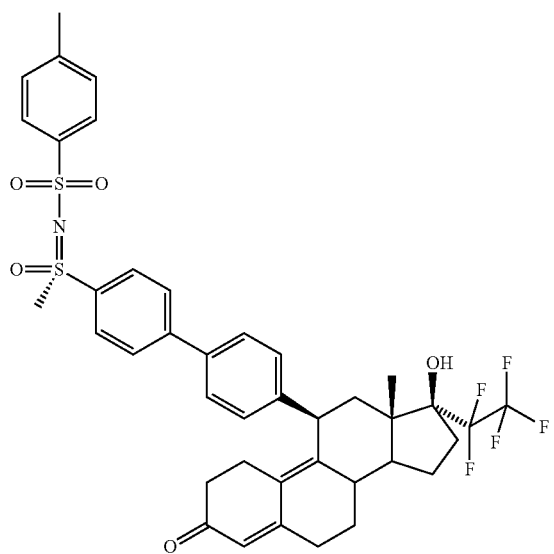 [SMILES: Cc1ccc(S(=O)(=O)N=[S@](C)(=O)c2ccc(-c3ccc([C@H]4C[C@@]5(C)C(CC[C@@]5(O)C(F)(F)C(F)(F)F)C5CCC6=CC(=O)CCC6=C54)cc3)cc2)cc1]

a) N-[{4'-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxane]-11-yl]biphenyl-4-yl}(RS)(methyl)-λ⁴-sulphanylidene]-4-methylbenzene sulphonamide

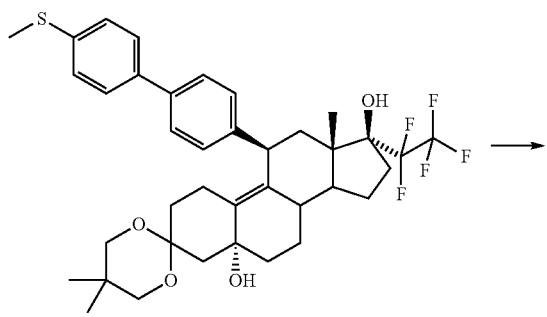

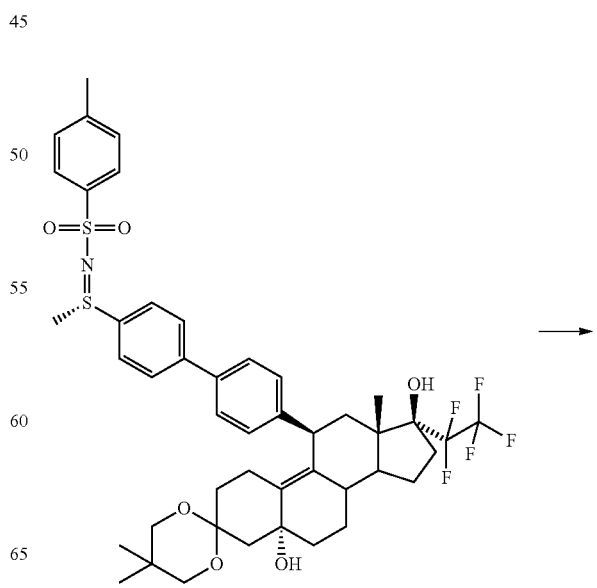

31

-continued

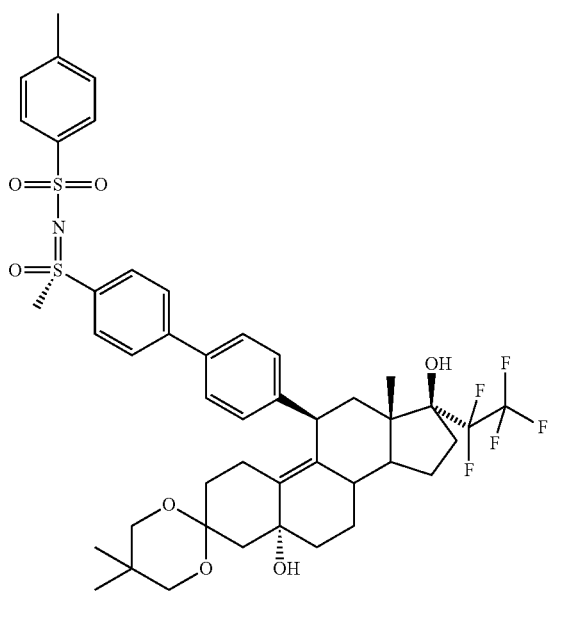

As in example 7b), 638 mg of the title compound was obtained from 709 mg of the compound obtained in example 11a) by reaction with 30% hydrogen peroxide solution and sodium carbonate in a mixture of acetonitrile and methanol.

$^1$H-NMR (300 MHz, CDCl$_3$): δ=8.04 d (2H); 7.87 d (2H); 7.78 d (2H); 7.50 d (2H); 7.35 d (2H); 7.27 d (2H); 4.46 s (1H); 4.40 dbr (1H); 3.40-3.60 m (4H); 3.46 s (3H); 2.39 s (3H); 1.07 s (3H); 0.87 s (3H); 0.56 s (3H) (mixture of diastereomers).

c) N-[{4'-[(11β,17β)-17-hydroxy-3-oxo-17-(pentafluoroethyl)estra-4,9-dien-11-yl]biphenyl-4-yl}(RS)(methyl)-oxido-λ$^6$-sulphanylidene]-4-methylbenzene sulphonamide

32

-continued

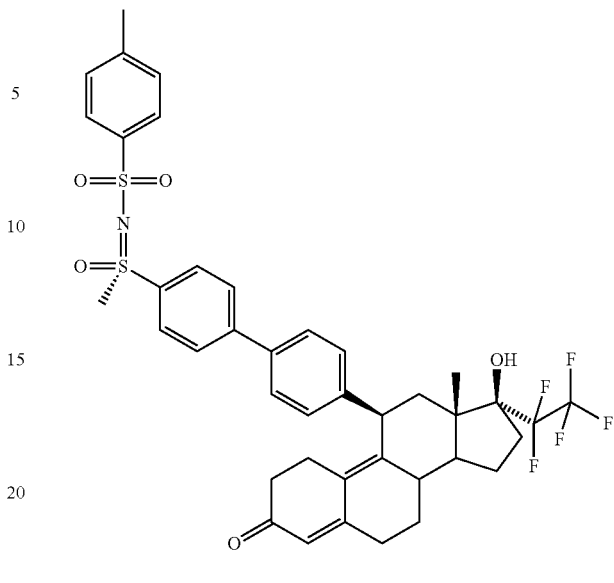

As in example 1c), 523 mg of the title compound was prepared from 633 mg of the compound prepared in 11 b) by reaction with semi-concentrated sulphuric acid in methanol.

$^1$H-NMR (300 MHz, CDCl$_3$): δ=8.06 d (2H); 7.87 d (2H); 7.78 d (2H); 7.52 d (2H); 7.20-7.35 m (4H); 5.80 sbr (1H); 4.51 dbr (1H); 3.45 s (3H); 2.39 s (3H); 0.62 s (3H) (mixture of diastereomers).

EXAMPLE 12

(11β,17β)-17-hydroxy-11-[4'-(RS-methylsulphonimidoyl)biphenyl-4-yl]-17-(pentafluoroethyl)estra-4,9-dien-3-one

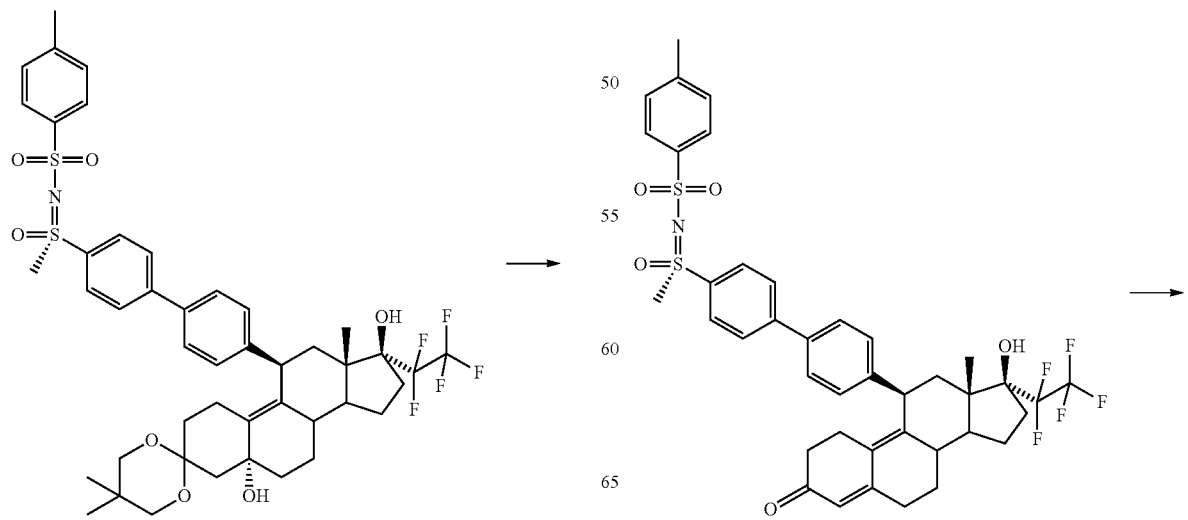

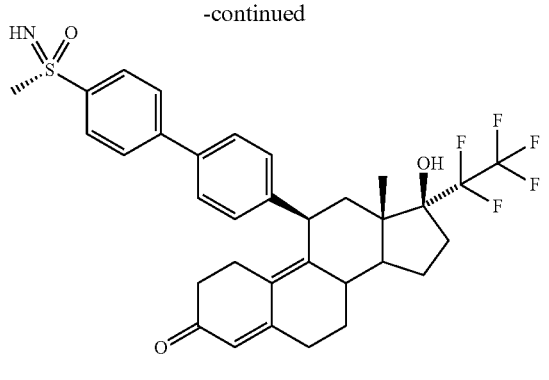

As in example 8, 325 mg of the title compound was obtained from 500 mg of the compound prepared in example 11c) by reaction with concentrated sulphuric acid in chloroform.

$^1$H-NMR (300 MHz, CDCl$_3$): δ=8.07 d (2H); 7.74 d (2H); 7.55 d (2H); 7.30 d (2H); 5.80 sbr (1H); 4.51 dbr (1H); 3.15 s (3H); 0.64 s (3H) (mixture of diastereomers).

EXAMPLE 13

(11β,17β)-17-hydroxy-17-(pentafluoroethyl)-11-(4'-sulphanylbiphenyl-4-yl)estra-4,9-dien-3-one

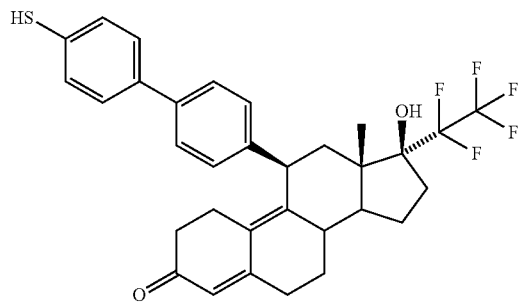 [SMILES: C[C@]12C[C@H](c3ccc(-c4ccc(S)cc4)cc3)C3=C4CCC(=O)C=C4CCC3C1CC[C@@]2(O)C(F)(F)C(F)(F)F]

a) (5R,8S,11R,13S,14S,17S)-5',5',13-trimethyl-17-(pentafluoroethyl)-11-(4'-sulphanylbiphenyl-4-yl)-1,2,6,7,8,11,12,13,14,15,16,17-dodecahydrospiro[cyclopenta[a]phenanthrene-3,2'-[1,3]dioxane]-5,17(4H)-diol

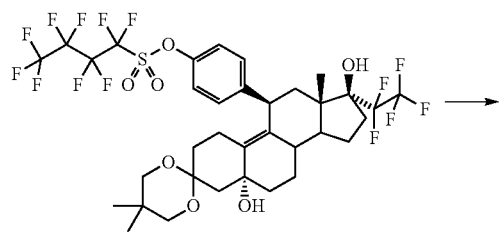

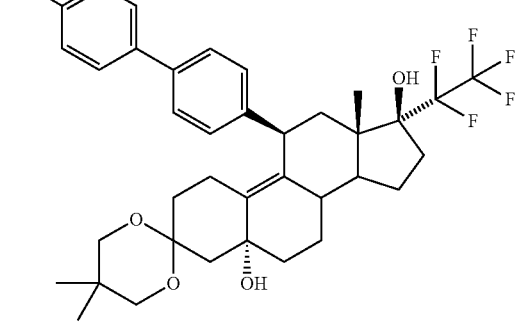

As in example 9d), 478 mg of the title compound was prepared from 1 g of the compound described in example 9c) and (4-mercaptophenyl)boronic acid in the presence of tetrakis(triphenylphosphine)palladium, lithium chloride, 2-molar aqueous sodium carbonate solution in a mixture of toluene and ethanol.

$^1$H-NMR (400 MHz, CDCl$_3$): δ=7.14-7.32 m (8H); 4.42 s (1H); 4.30 dbr (1H); 3.40-3.60 m (4H); 1.05 s (3H); 0.88 s (3H); 0.54 s (3H).

b) (11β,17β)-17-hydroxy-17-(pentafluoroethyl)-11-(4'-sulphanylbiphenyl-4-yl)estra-4,9-dien-3-one

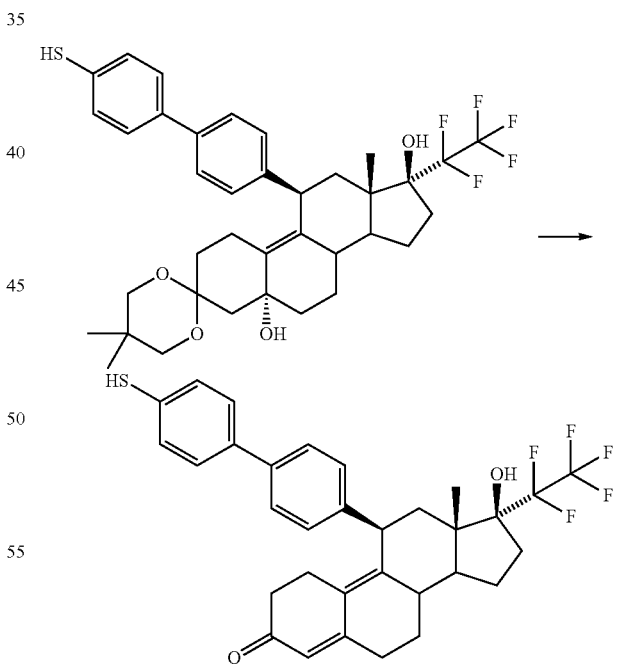

As in example 1c), 103 mg of the title compound was prepared from 200 mg of the compound prepared in 13a) by reaction with semi-concentrated sulphuric acid in methanol.

$^1$H-NMR (400 MHz, CDCl$_3$): δ=7.20-7.38 m (6H); 7.11d (2H); 5.78 sbr (1H); 4.42 dbr (1H); 0.61 s (3H).

EXAMPLE 14

4'-[(11β,17β)-17-hydroxy-3-oxo-17-(pentafluoro-ethyl)estra-4,9-dien-11-yl]-N,N-dimethylbiphenyl-4-sulphonamide

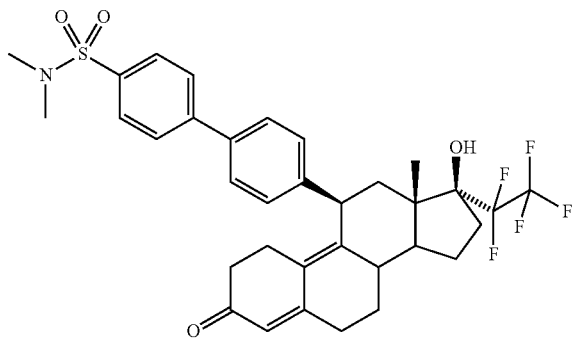 [SMILES: CN(C)S(=O)(=O)c1ccc(-c2ccc([C@H]3C[C@@]4(C)C(CC[C@@]4(O)C(F)(F)C(F)(F)F)C4CCC5=CC(=O)CCC5=C43)cc2)cc1]

a) 4'-[(5R,8S,11R,13S,14S,17S)-5,17-dihydroxy-5', 5',13-trimethyl-17-(pentafluoroethyl)-1,2,4,5,6,7,8, 11,12,13,14,15,16,17-tetradecahydrospiro[cyclopenta[a]phenanthrene-3,2'-[1,3]dioxane]-11-yl]-N,N-dimethylbiphenyl-4-sulphonamide

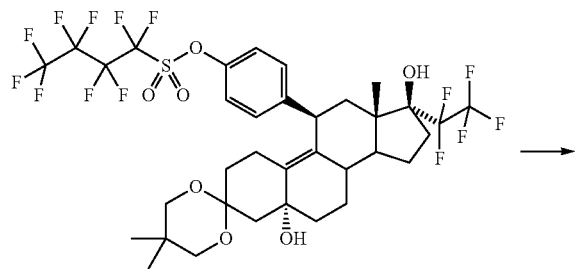

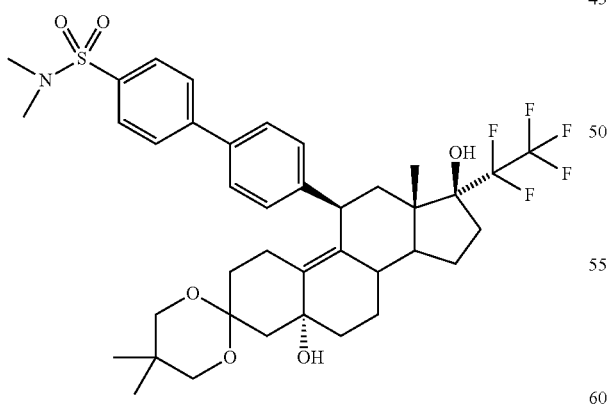

As in example 9d), 235 mg of the title compound was prepared from 300 mg of the compound described in example 9c) and [4-[(dimethylamino)sulphonyl]phenyl]boronic acid in the presence of tetrakis(triphenylphosphine) palladium, lithium chloride, 2-molar aqueous sodium carbonate solution in a mixture of toluene and ethanol.

$^1$H-NMR (300 MHz, CDCl$_3$): δ=7.83 d (2H); 7.73 d (2H); 7.52 d (2H); 7.33 d (2H); 4.47 s (1H); 4.39 dbr (1H); 3.40-3.60 m (4H); 2.75 s (6H); 1.06 s (3H); 0.88 s (3H); 0.57 s (3H).

b) 4'-[(11β,17β)-17-hydroxy-3-oxo-17-(pentafluoroethyl)estra-4,9-dien-11-yl]-N,N-dimethylbiphenyl-4-sulphonamide

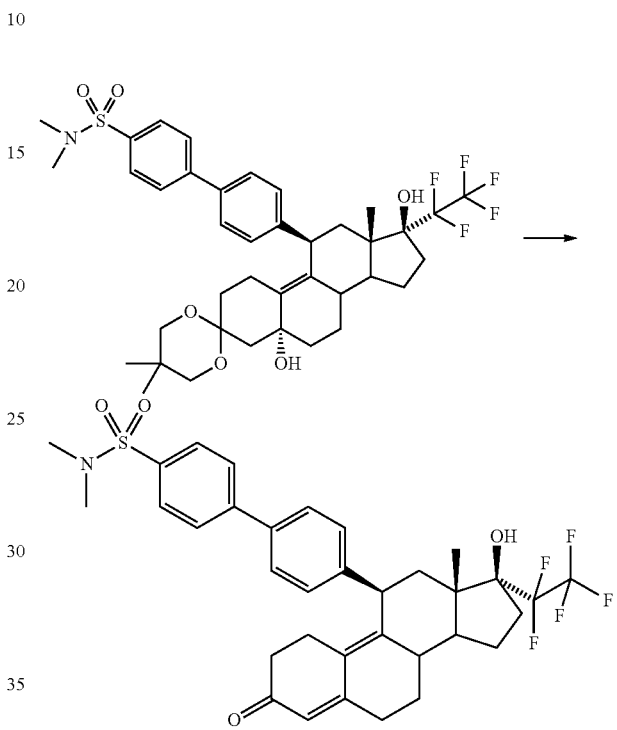

As in example 1c), 113 mg of the title compound was prepared from 230 mg of the compound prepared in 14a) by reaction with semi-concentrated sulphuric acid in methanol.

$^1$H-NMR (400 MHz, CDCl$_3$): δ=7.83 d (2H); 7.72 d (2H); 7.55 d (2H); 7.30 d (2H); 5.80 sbr (1H); 4.52 dbr (1H); 2.75 s (6H); 0.64 s (3H).

EXAMPLE 15

4-[(11β,17β)-17-Hydroxy-3-oxo-17-(pentafluoro-ethyl)estra-4,9-dien-11-yl]-N,N-dimethylbenzene sulphonamide

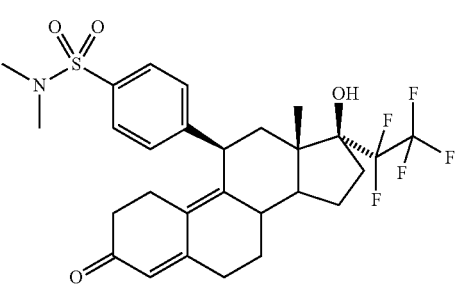 [SMILES: CN(C)S(=O)(=O)c1ccc([C@H]2C[C@@]3(C)C(CC[C@@]3(O)C(F)(F)C(F)(F)F)C3CCC4=CC(=O)CCC4=C32)cc1]

a) 4-[(5R,8S,11R,13S,14S,17S)-5,17-Dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl]-N,N-dimethylbenzene sulphonamide b) 4-[(11β,17β)-17-Hydroxy-3-oxo-17-(pentafluoroethyl)estra-4,9-dien-11-yl]-N,N-dimethylbenzene sulphonamide

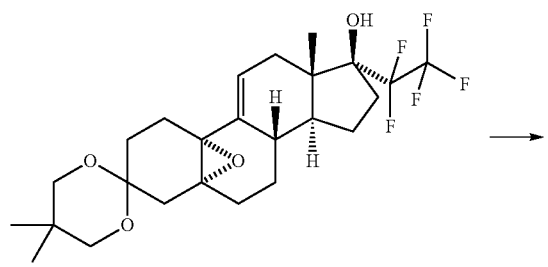

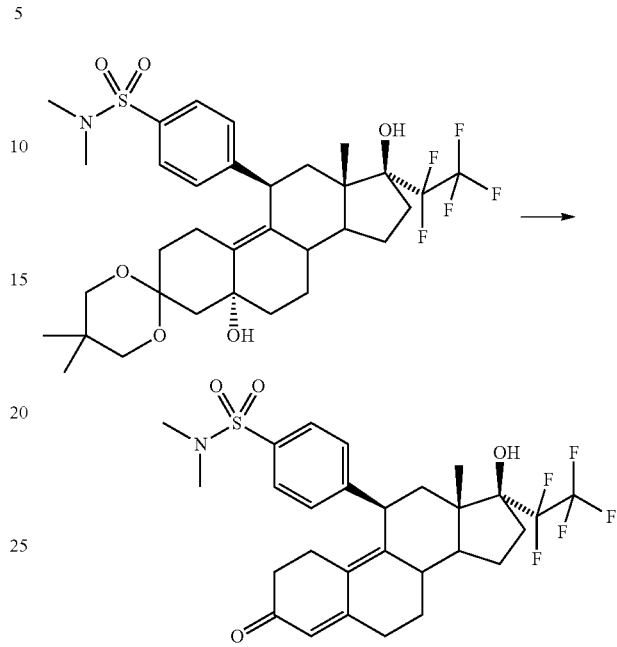

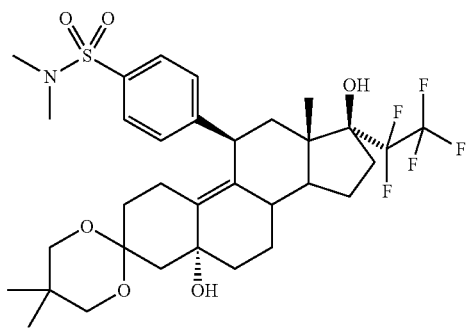

5.1 ml of a 2-molar solution of diisopropylmagnesium chloride in diethyl ether was diluted with 10 ml THF, with cooling (−10° C.). Then 8.12 ml of a 2.5-molar solution of n-butyllithium in hexane was added dropwise at −10° C. in the space of 30 minutes. It was stirred for a further 2 hours and then 15.1 mg CuCl was added. After stirring for a further 5 minutes, a solution of 500 mg of the substance described in example 1a) in 5 ml THF was added. It was stirred for a further 3 hours at −10° C. and then heated slowly to 23° C. It was stirred for a further 12 hours at 23° C. Then saturated aqueous NH$_4$Cl solution was added to the reaction mixture, with external cooling. It was stirred for a further 30 minutes and then extracted several times with ethyl acetate. The combined organic phases were washed with saturated sodium chloride solution and dried over sodium sulphate. The raw product was purified by silica gel chromatography. This gave 214 mg of the title compound.

$^1$H-NMR (300 MHz, CDCl$_3$): δ=7.65 d (2H); 7.40 d (2H); 4.45 s (1H); 4.38 dbr (1H); 3.40-3.60 m (4H); 2.69 s (6H); 1.03 s (3H); 0.89 s (3H); 0.49 s (3H).

As in example 1c), 74 mg of the title compound was prepared from 100 mg of the compound prepared in 15a) by reaction with semi-concentrated sulphuric acid in methanol.

$^1$H-NMR (400 MHz, CDCl$_3$): δ=7.69 d (2H); 7.38 d (2H); 5.80 sbr (1H); 4.04 dbr (1H); 2.68 s (6H); 0.52 s (3H)

EXAMPLE 16

Progesterone Receptor-Antagonistic Action in Stable Transfectants of Human Neuroblastoma Cells (SK-N-MC Cells) with the Human Progesterone a or Progesterone B Receptor and an MTV-LUC Reporter Construct SK-N-MC cells (human neuroblastoma cells), which have been stably transfected with plasmids, which express the human progesterone receptor B (pRChPR-B-neo) or the human progesterone receptor A (pRChPR-A-neo) and a reporter construct (pMMTV-LUC), were incubated for 24 hours either in the absence (negative control) or in the presence of increasing amounts of the respective test compound (0.01 nmol/l, 0.1 nmol/l, 1 nmol/l, 10 nmol/l, 100 nmol/1 and 1 μmol/l), in order to determine the agonistic efficacy. As positive control of reporter gene induction, the cells were treated with the synthetic gestagen promegestone (0.01 nmol/l, 0.1 nmol/l, 1 nmol/l, 10 nmol/l, 100 nmol/1 and 1 μmol/l). For determination of the antagonistic activity, the cells were treated with 0.1 nmol/1 promegestone and additionally with increasing amounts of the respective test compound (0.01 nmol/l, 0.1 nmol/l, 1 nmol/l, 10 nmol/l, 100 nmol/1 and 1 μmol/l). The activity of the LUC reporter gene (LUC=luciferase) was determined in the cell lysates and was measured as RLU (relative light units). All measured values are given as percentage efficacy and as EC$_{50}$ or IC$_{50}$ concentrations.

11β,-(4-Acetylphenyl)-20,20,21,21,21-pentafluoro-17-hydroxy-19-nor-17α-pregna-4,9-dien-3-one and 20,20,21, 21,21-pentafluoro-17-hydroxy-11β-[4-(hydroxyacetyl)phenyl]-19-nor-17α-pregna-4,9-dien-3-one, very potent and therefore preferred examples from WO98/34947 and WO2008/058767, were tested as comparative compounds along with the test compound.
a) Agonistic Activity:
None of the stated test compounds shows agonistic activity.
b) Antagonistic Activity:
All of the stated compounds show 100% antagonistic efficacy.
The antagonistic efficacy of the compounds is presented in Table 1.

|  | Progesterone receptor A (PR-A) | | Progesterone receptor B (PR-B) | |
| --- | --- | --- | --- | --- |
| Compound | Potency $IC_{50}$ [nmol/l] | Efficacy [%] | Potency $IC_{50}$ [nmol/l] | Efficacy [%] |
| 11β-(4-Acetylphenyl)-20,20,21,21,21-pentafluoro-17-hydroxy-19-nor-17α-pregna-4,9-dien-3-one | 0.014 | 100 | 0.02 | 100 |
| 20,20,21,21,21-Pentafluoro-17-hydroxy-11β-[4-(hydroxyacatyl)phenyl]-19-nor-17α-pregna-4,9-dien-3-one dien-3-one | 0.18 | 100 | 0.28 | 100 |
| Example 1 | 0.011 | 100 | 0.012 | 100 |
| Example 2 | 0.01 | 100 | 0.01 | 100 |
| Example 3 | 0.11 | 100 | 0.12 | 100 |
| Example 4 | 0.096 | 100 | 0.087 | 100 |
| Example 5 | 0.1 | 100 | 0.09 | 100 |
| Example 6 | 0.2 | 100 | 0.23 | 100 |
| Example 7 | 1.0 | 100 | 0.8 | 100 |
| Example 8 | 0.9 | 100 | 0.9 | 100 |
| Example 9 | 0.01 | 100 | 0.01 | 100 |
| Example 10 | 0.011 | 100 | 0.013 | 100 |
| Example 11 | 0.01 | 100 | 0.01 | 100 |
| Example 12 | 0.08 | 100 | 0.08 | 100 |
| Example 13 | 0.072 | 100 | 0.072 | 100 |
| Example 14 | 0.01 | 100 | 0.01 | 100 |
| Example 15 | 0.1 | 100 | 0.2 | 100 |

EXAMPLE 17

Abortion Test on Female Rats

The action of progesterone and of the progesterone receptor is a fundamental precondition for successful pregnancy or gestation in mammals. The progesterone-antagonistic action of the compounds according to the invention was tested on pregnant rats (6 rats per group) on day 5 to 7 post coitum with conventional housing and feeding conditions.

After successful hand mating, the pregnant animals (presence of sperm in the vaginal smear on day 1 of pregnancy=d1 p.c.) were randomized and divided into the treatment group and the control group. The animals then each received subcutaneously or orally 0.15; 0.5; 1.5 or 5 mg/kg of the test compound or 1.0 ml/kg of vehicle (benzyl benzoate/castor oil: 1+4 [v/v]) daily from day 5 to day 7 (d5-d7 p.c.).

Autopsy was carried out on day 9 (d9 p.c.). As a characteristic of progesterone receptor antagonistic action, the uterus was examined for the presence of nidation sites. Complete absence, or also the presence of pathological, haemorrhagic or otherwise abnormal nidation sites on day 9 (d9 p.c.) was assessed as abortion. The results of the tests are shown in Table 3.

TABLE 3

Results for the rat (termination of early pregnancy)

| Test compound according to | Daily dose [mg/kg] s.c. or p.o. | Abortion rate [%] |
| --- | --- | --- |
| Vehicle |  | 0 |
| Example 1 | 0.5 | 80 |
| (11β,17β)-17-hydroxy-11-[4-(methylsulphanyl)phenyl]-17-(pentafluoroethyl)estra-4,9-dien-3-one | 1.5 | 100 |
|  | 5.0 | 100 |

TABLE 3-continued

Results for the rat (termination of early pregnancy)

| Test compound according to | Daily dose [mg/kg] s.c. or p.o. | Abortion rate [%] |
| --- | --- | --- |
| Example 4 | 0.15 | 40 |
| (11β,17β)-17-hydroxy-11-[4-(methylsulphonyl)phenyl]-17-(pentafluoroethyl)estra-4,9-dien-3-one | 0.5 | 100 |
|  | 1.5 | 100 |
|  | 5.0 | 100 |
| Example 8 | 0.15 | 40 |
| (11β,17β)-17-hydroxy-11-[4-(RS-methylsulphonimidoyl)-phenyl]-17-(pentafluoroethyl)estra-4,9-dien-3-one | 0.5 | 100 |
|  | 1.5 | 100 |
|  | 5.0 | 100 |

EXAMPLE 18

Metabolic stability of (11β,17β)-17-hydroxy-11-[4-(methylsulphonyl)phenyl]-17-(pentafluoroethyl)estra-4,9-dien-3-one and (11β,17β)-17-hydroxy-11-[4'-(methylsulphonyl)-biphenyl-4-yl]-17-(pentafluoroethyl)estra-4,9-dien-3-one in Human Liver Microsomes (HLM)

Isolated human liver microsomes (HLM) were used for assessing the metabolic stability of compounds of general formula I.

Incubations were carried out with 2.4 ml of HLM solution (0.5 mg/ml protein content), 30 μl of the test compound (final concentration 1 μM) and 0.6 ml of the cofactor mixture (=NADPH-generating system of 3 IU glucose-6-phosphate dehydrogenase, 14.6 mg glucose-6-phosphate, 1.2 mg NADP) at 37° C. in 100 mM phosphate buffer at pH 7.4. Samples are taken at 6 time points (2-60 min), precipitated with an equal volume of methanol and the recovery of the test substances used in the supernatant is determined by LC-MS/MS analysis. The intrinsic clearance of the substance in the liver microsome preparation can be calculated from the half-life found for the breakdown of the substance. Based on this, together with various physiological characteristics according to the well-stirred model, it is then possible to predict a (metabolic) in vivo clearance with respect to phase I reactions. The (metabolic) in vivo clearance in humans predicted correspondingly for the test compounds (11β,17β)-17-hydroxy-11-[4-(methylsulphonyl)phenyl]-17-(pentafluoroethyl)estra-4,9-dien-3-one and (11β,17β)-17-hydroxy-11-[4'-(methylsulphonyl)biphenyl-4-yl]-17-(pentafluoroethyl)-estra-4,9-dien-3-one was very low: 0.1 L/h/kg and <0.01 L/h/kg, respectively.

EXAMPLE 19

Permeation of (11β,17β)-17-hydroxy-11-[4-(methylsulphonyl)phenyl]-17-(pentafluoroethyl)estra-4,9-dien-3-one in Caco-2 cells For the permeation studies, Caco-2 cells with a cell count of 300000 cells/ml were cultivated on Transwell Clear filter inserts (polyester; pore size 0.4 μm) in 12-well cell culture plates for at least 14 days in cell culture medium (1.5 ml) at 37° C., 5% $CO_2$ and 95% air humidity. Before the test, to verify the "compactness" of the cell monolayer, the transepithelial resistance (TEER value) was determined, which must be greater than 300 Ωcm². Then the cell culture medium was replaced with hot transport buffer (0.5 ml apical, 1.5 ml basolateral) and the cells were equilibrated in it for 5 min. The permeability test was performed in duplicate at a substance concentration of 2 μM. At the start of the experiment, 100 μl (Ap0 min) was taken from the apical compartment and 100 μl of ice-cold stopping solution was added to it immediately. The filters were then incubated at 37° C. with gentle shaking for 90 min, then 100 μl was taken again from the apical side (Ap90 min) and 400 μl from the basolateral side (Bas90 min) and in each case the same volume of stopping solution was added. After further dilution of the samples with 4 times the volume of stopping solution/transport buffer (1+1) they were sedimented overnight at −20° C. and the supernatant was analysed by LCMS/MS. The Papp value of the substances was calculated from the following formula.

$$Papp = \frac{V_{res}}{A \cdot C_{t0,don}} \cdot \frac{\Delta C_{res}}{\Delta t}$$

$V_{res}$: buffer volume on the receptor side; A: filter area=1 cm²; $C_{t0,don}$: concentration of substance on the donor side; $\Delta C_{res}/\Delta t$: change in concentration of substance over time on the receptor side (11β,17β)-17-Hydroxy-11-[4-(methylsulphonyl)phenyl]-17-(pentafluoroethyl)estra-4,9-dien-3-one showed a very high permeation of 104 nm/s in this assay.

EXAMPLE 20

Investigation of the Action on the Cardiovascular System (Incl. ECG) of Anaesthetized Beagle Dogs (11β,17p)-17-Hydroxy-11-[4-(methylsulphonyl)phenyl]-17-(pentafluoroethyl)estra-4,9-dien-3-one, dissolved in a mixture of PEG 400 and HP-β-CD (60% PEG 400, 40% HP-β-CD 30%), was administered intravenously to anaesthetized female beagle dogs. The body weight of the dogs was >9 kg. 3 dogs were treated per group and additionally 3 dogs in the control group. 0.1; 0.33 and 1 mg/kg of the substance was administered in 3 consecutive infusions, in each case over a period of 30 minutes. The maximum amount of vehicle was 0.4 ml per kg for 30 minutes. Blood samples were taken from the animals at various time points. The highest plasma level (average for all 3 animals) was 1650 ng/ml at the end of the third infusion.

In the tested dose range, in comparison with the control, no biologically relevant effects on the cardiovascular system (pulmonary artery pressure, systemic arterial blood pressure, heart rate, ECG) were observed.

The invention claimed is:
1. A compound of formula I

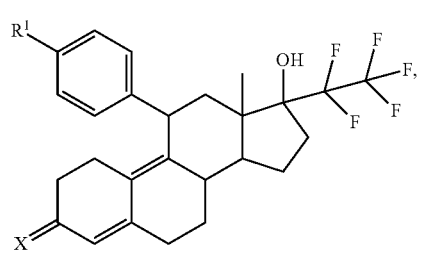

in which
R¹ stands either for a residue Y or for a phenyl ring substituted once or twice with a residue Y,
Y is $S(O)(NH)R^3$ or $S(O)_2NR^9R^{10}$,
R³ stands for $C_1$-$C_6$-alkyl,
X denotes an oxygen atom,
R⁹, R¹⁰ independently of one another are each hydrogen, $C_1$-$C_6$-alkyl or aryl where aryl is phenyl or a stereoisomer or a salt, thereof.
2. The compound according to claim 1, in which R¹ represents $S(O)(NH)R^3$ and X represents O and the separate stereoisomers thereof.
3. The compound according to claim 2, in which R³ represents $C_1$-$C_6$-alkyl and the separate stereoisomers thereof.
4. The compound according to claim 3, in which R³ represents methyl and the separate stereoisomers thereof.
5. The compound according to claim 1, in which R³ represents $C_1$-$C_6$-alkyl.
6. A compound according to claim 1 selected from the group consisting of:
(11β, 17β)-17-hydroxy-11-[4-(RS-methylsulphonimidoyl)phenyl]-17-(pentafluoroethyl)estra-4,9-dien-3-one;
(11β, 17β)-17-hydroxy-11-[4'-(RS-methylsulphonimidoyl)biphenyl-4-yl]-17-(pentafluoroethyl)estra-4,9-dien-3-one;

4'-[(11β, 17β)-17-hydroxy-3-oxo-17-(pentafluoroethyl) estra-4,9-den-11-yl]-N,N-dimethylbiphenyl-4-sulphonamide; and 4-[(11β, 17β)-17-hydroxy-3-oxo-17-(pentafluoroethyl) estra-4,9-dien-11-yl]-N,N-dimethylbenzene sulphonamide.

7. A pharmaceutical composition comprising a compound as defined in claim 1 and another active substance.

8. A pharmaceutical composition comprising a compound as defined in claim 1 and an inert, non-toxic, pharmaceutically suitable excipient.

9. A method of treatment of heavy menstrual bleeds, meningiomas, or for fertility control, comprising administering to a subject in need thereof an effective amount of a compound of claim 1.

10. A method of treatment of fibroids of the uterus comprising administering to a subject in need thereof an effective amount of a compound of claim 1.

11. A method of treatment of endometriosis comprising administering to a subject in need thereof an effective amount of a compound of claim 1.

12. A method of treatment of heavy menstrual bleeds, meningiomas, hormone-dependent breast cancers or for fertility control comprising administering to a subject in need thereof an effective amount of a pharmaceutical composition of claim 7.

13. A method of treatment of fibroids of the uterus comprising administering to a subject in need thereof an effective amount of a pharmaceutical composition of claim 7.

14. A method of treatment of endometriosis comprising administering to a subject in need thereof an effective amount of a pharmaceutical composition of claim 7.

* * * * *